(12) United States Patent
Mann et al.

(10) Patent No.: US 11,642,391 B2
(45) Date of Patent: May 9, 2023

(54) COMPOSITIONS CONTAINING A PHARMACOPHORE WITH SELECTIVITY TO DISEASED TISSUE AND METHODS OF MAKING SAME

(71) Applicants: Vascular BioSciences, San Diego, CA (US); Sanford Burnham Prebys Medical Discovery Institute, La Jolla, CA (US); David Mann, San Diego, CA (US); Erkki Ruoslahti, La Jolla, CA (US); Masanobu Komatsu, La Jolla, CA (US)

(72) Inventors: David Mann, San Diego, CA (US); Erkki Ruoslahti, La Jolla, CA (US); Masanobu Komatsu, La Jolla, CA (US)

(73) Assignee: Vascular Biosciences, San Diego, CA (US)

( * ) Notice: Subject to any disclaimer, the term of this patent is extended or adjusted under 35 U.S.C. 154(b) by 959 days.

(21) Appl. No.: 15/502,170

(22) PCT Filed: Aug. 4, 2015

(86) PCT No.: PCT/US2015/043686
§ 371 (c)(1),
(2) Date: Feb. 6, 2017

(87) PCT Pub. No.: WO2016/022610
PCT Pub. Date: Feb. 11, 2016

(65) Prior Publication Data
US 2019/0022170 A1 Jan. 24, 2019

Related U.S. Application Data

(60) Provisional application No. 62/161,121, filed on May 13, 2015, provisional application No. 62/034,046, filed on Aug. 6, 2014.

(51) Int. Cl.

| | | |
|---|---|---|
| A61K 38/12 | (2006.01) | |
| G16B 35/00 | (2019.01) | |
| G16C 20/60 | (2019.01) | |
| A61K 31/337 | (2006.01) | |
| A61K 31/506 | (2006.01) | |
| A61K 38/55 | (2006.01) | |
| A61K 45/06 | (2006.01) | |
| A61K 31/222 | (2006.01) | |
| A61K 31/573 | (2006.01) | |

(Continued)

(52) U.S. Cl.
CPC .............. *A61K 38/12* (2013.01); *A61K 31/18* (2013.01); *A61K 31/222* (2013.01); *A61K 31/337* (2013.01); *A61K 31/436* (2013.01); *A61K 31/438* (2013.01); *A61K 31/506* (2013.01); *A61K 31/573* (2013.01); *A61K 38/08* (2013.01); *A61K 38/55* (2013.01); *A61K 45/06* (2013.01); *A61K 47/64* (2017.08); *A61K 47/643* (2017.08); *A61K 47/6811* (2017.08); *A61K 47/6851* (2017.08); *A61P 1/16* (2018.01); *A61P 9/12* (2018.01); *A61P 11/00* (2018.01); *A61P 13/12* (2018.01); *A61P 31/00* (2018.01); *A61P 35/00* (2018.01); *G01N 33/15* (2013.01); *G01N 33/5008* (2013.01); *G16B 35/00* (2019.02); *G16B 35/10* (2019.02); *G16B 35/20* (2019.02); *G16C 20/60* (2019.02)

(58) Field of Classification Search
CPC .... A61K 38/12; A61K 31/337; A61K 31/506; A61K 38/55; A61K 45/06; A61K 31/222; A61K 31/573; A61K 47/6851; A61K 47/643; A61K 47/6811; A61K 47/64; A61K 31/18; A61K 31/436; A61K 31/438; A61K 38/08; A61K 2300/00; G16B 35/00; G16B 35/20; G16B 35/10; G16C 20/60; G01N 33/15; G01N 33/5008; A61P 31/00; A61P 1/16; A61P 9/12; A61P 13/12; A61P 11/00; A61P 35/00

See application file for complete search history.

(56) References Cited

U.S. PATENT DOCUMENTS

| | | |
|---|---|---|
| 2005/0053978 A1 | 3/2005 | Maynard |
| 2011/0165064 A1 | 7/2011 | Ruoslahti et al. |

(Continued)

FOREIGN PATENT DOCUMENTS

| | | |
|---|---|---|
| WO | 2007087266 | 8/2007 |
| WO | 2012118778 | 9/2012 |

OTHER PUBLICATIONS

Jarvinen et al, Molecular Changes in the Vasculature of Injured Tissues, The American Journal of Pathology, 2007, 171, pp. 702-711.*

(Continued)

*Primary Examiner* — Li N Komatsu
(74) *Attorney, Agent, or Firm* — Lewis Kohn & Walker LLP; David M. Kohn; Kari Moyer-Henry

(57) ABSTRACT

Compositions and methods useful for delivery of targeted therapies for pulmonary arterial hypertension, sepsis, cancer and cachexia. The compositions and methods are based on peptide pharmacophores that selectively bind to and home to diseased tissue and enable targeted therapies to affect a beneficial therapeutic result. Peptide pharmacophores may selectively target tumor vasculature, regenerating tissue, wounded tissue, inflamed tissue, fibrotic tissue, remodeled tissue, tissue characterized by elevated heparanase levels, and have the ability to internalize into such diseased cells.

2 Claims, 25 Drawing Sheets
Specification includes a Sequence Listing.

(51) Int. Cl.
| | |
|---|---|
| A61K 47/68 | (2017.01) |
| A61K 47/64 | (2017.01) |
| G01N 33/15 | (2006.01) |
| G16B 35/20 | (2019.01) |
| G16B 35/10 | (2019.01) |
| A61P 31/00 | (2006.01) |
| A61P 1/16 | (2006.01) |
| A61P 9/12 | (2006.01) |
| A61P 13/12 | (2006.01) |
| A61P 11/00 | (2006.01) |
| A61P 35/00 | (2006.01) |
| A61K 31/18 | (2006.01) |
| A61K 31/436 | (2006.01) |
| A61K 31/438 | (2006.01) |
| A61K 38/08 | (2019.01) |
| G01N 33/50 | (2006.01) |

(56) References Cited

U.S. PATENT DOCUMENTS

2011/0262347 A1   10/2011   Ruoslahti et al.
2012/0201753 A1    9/2012   Ruoslahti et al.
2013/0058993 A1    7/2013   Ruoslahti et al.

OTHER PUBLICATIONS

Blast search results for SEQ ID Nos. 24 and 29, from https://blast.ncbi.nlm.nih.gov/Blast.cgi, Sep. 28, 2020, pp. 1-16.*

Insulin [Homo sapiens], from http://www.ncbi.nlm.nih.goV/protein/AAA59172.1, p. 1, accessed May 12, 2014.*

Lewis et al, The Immunopathology of Sepsis: Pathogen Recognition, Systemic Inflammation, the Compensatory Anti-Inflammatory Response, and Regulatory T Cells, J Vet Intern Med, 2012, 26, pp. 457-482.*

Hayakawa etal, Sivelestat (Selective Neutrophil Elastase Inhibitor) Improves the Mortality Rate of Sepsis Associated With Both Acute Respiratory Distress Syndrome and Disseminated Intravascular Coagulation Patients, Shock, 2010, 33, pp. 14-18.*

Yang et al. "Pharmacophore modeling and applications in drug discovery: challenges and recent advances." Drug Discovery Today (2010) 15(11-12): 444-450.

Dror et al. "Predicting Molecular Interactions in silico: I. A Guide to Pharmacophore Identification and its Applications to Drug Design." Current Medicinal Chemistry (2004) 11:71-90.

Wang et al. "Design checkpoint kinase 2 inhibitors by pharmacophore modeling and virtual screening techniques." Bioorganic & Medicinal Chemistry Letters (2013) 23:6286-6291.

Jia et al. "Automated Pharmacophore Query Optimization with Genetic Algorithms—A Case Study Using the MC4R System." J. Chem. Inf. Model. (2007) 47:1545-1552.

Lynch et al. "Identification of Novel Activators of Constitutive Androstane Receptor from FDA-Approved Drugs by Integrated Computational and Biological Approaches." Pharm. Res. (2013) 30:489-501.

Dotti. "The Other Face of Chimeric Antigen Receptors." Molecular Therapy (2014) 22(5):899-900.

Banerjee et al. "Targeting xenobiotic receptors PXR and CAR in human diseases." Drug Discovery Today (2014) 20 (5): 618-628.

* cited by examiner

Figure 1.

| Sequence ID Number (SEQ ID NO) | Full Length Modified Sequence | Permuted Residues (bold) |
|---|---|---|
| 1 | C A R S K N K D C | RKK |
| 2 | C A R S R N K D C | RRK |
| 3 | C A R S K N R D C | RKR |
| 4 | C A R S R N R D C | RRR |
| 5 | C A K S R N K D C | KRK |
| 6 | C A K S K N R D C | KKR |
| 7 | C A K S K N K D C | KKK |
| 8 | C A K S R N R D C | KRR |

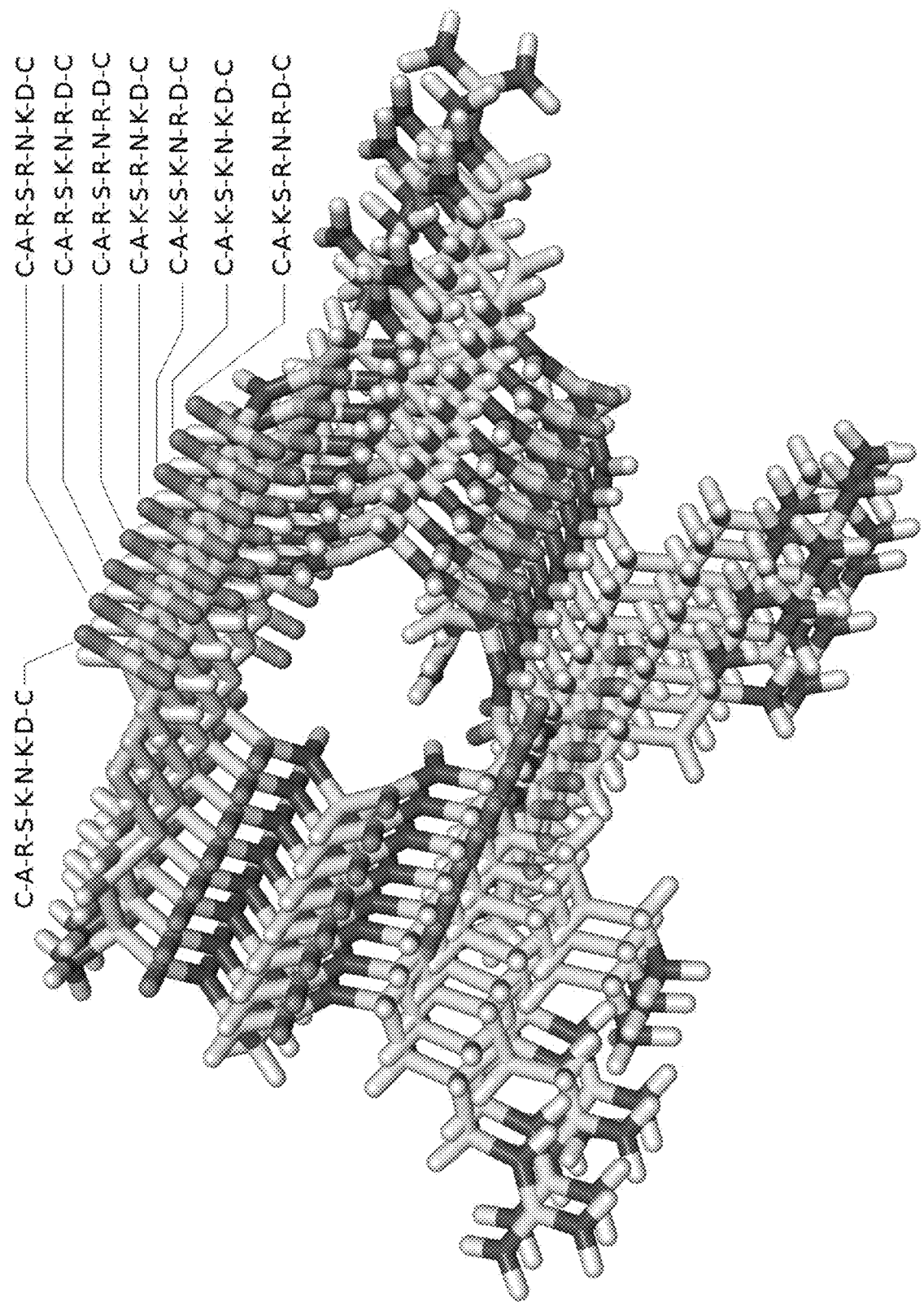
Figure 4. SEQ ID NOS: 1-8.

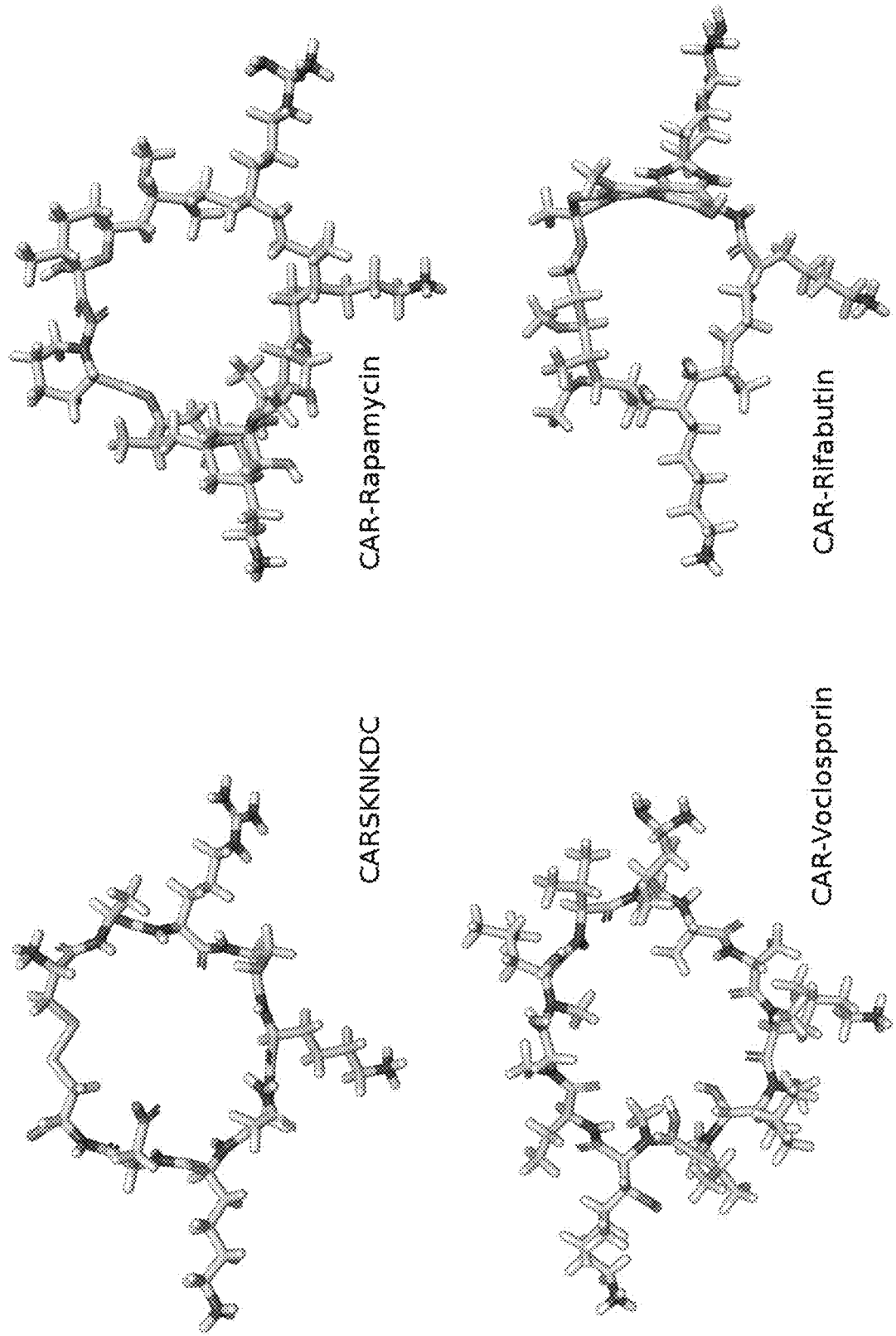
Figure 5. SEQ ID NO:1 (CAR Peptide) and SEQ ID NOS: 9-11 (CAR-Rifabutin, CAR-Rapamycin, and CAR-Voclosporin).

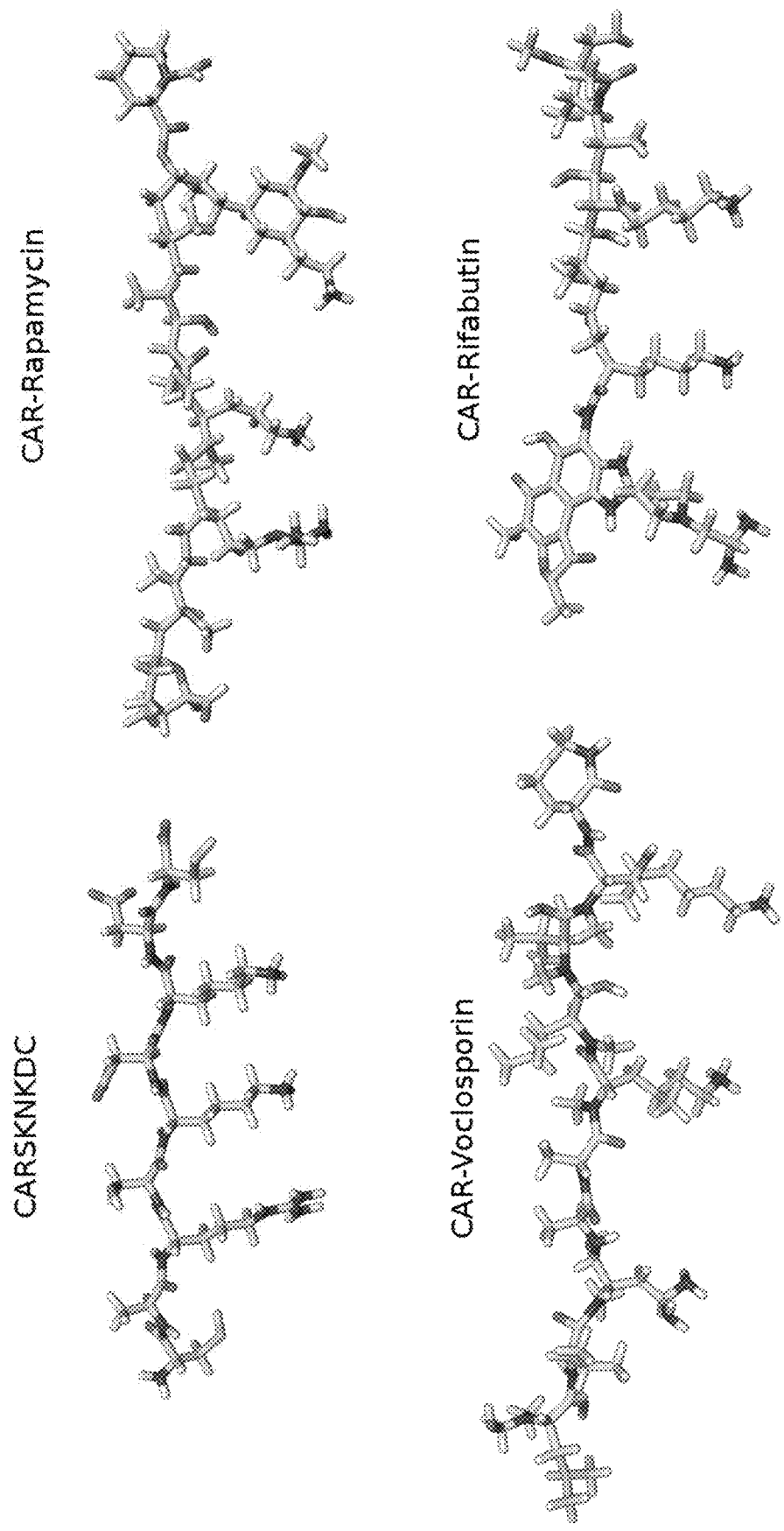
Figure 6. SEQ ID NO: 12 (Linear 9 amino acid CAR) and SEQ ID NOS: 13-15 (linear CAR-Rifabutin, linear CAR-Rapamycin, and linear CAR-Voclosporin).

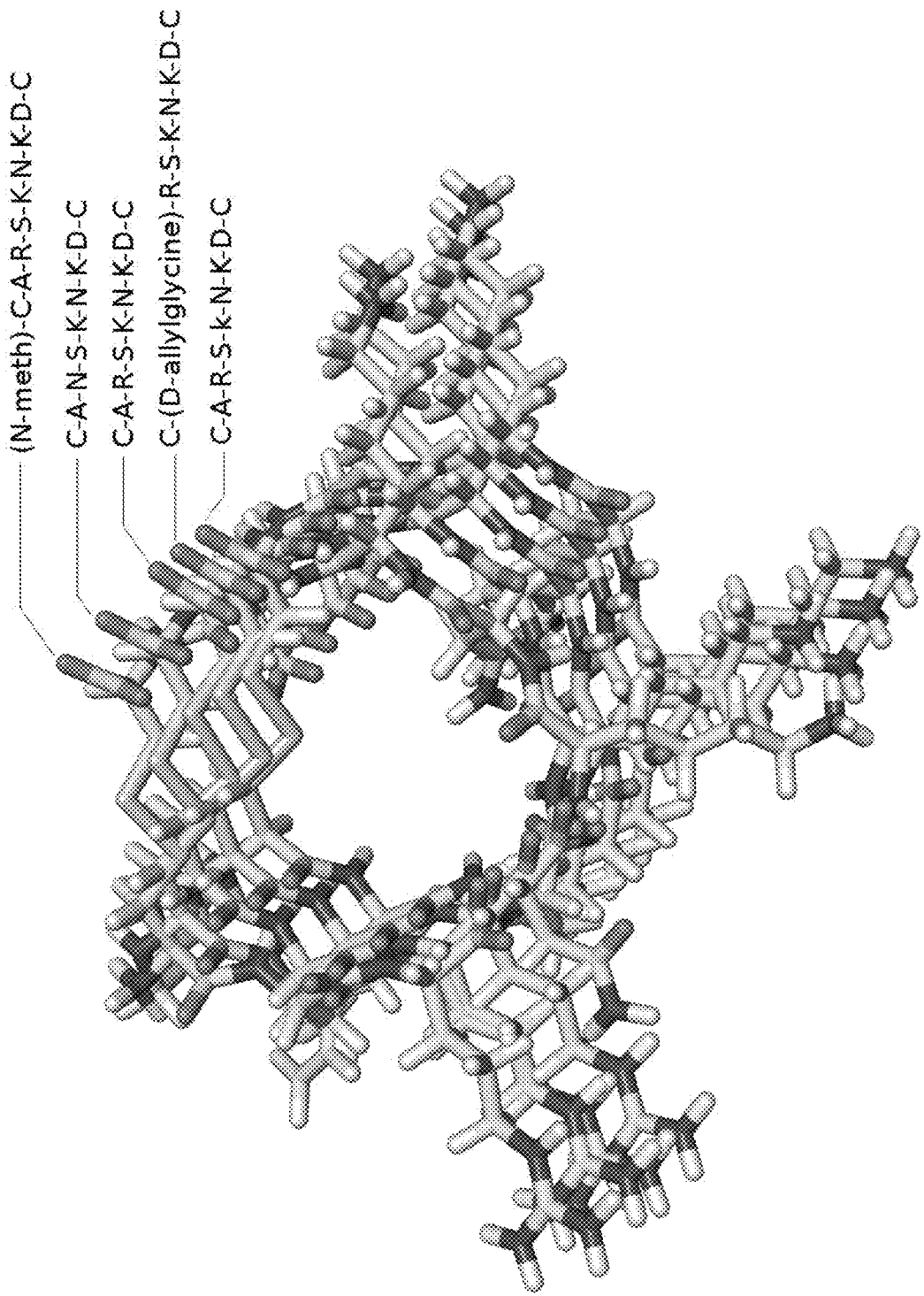
Figure 7. SEQ ID NO: 1 (CAR Peptide) and SEQ ID NOS: 16-19 (C A R S K N K D C, C-(D-allylglycine)-R-S-K-N-K-D-C, C A N S K N K D C, (N-meth)-C-A-R-S-K-N-K-D-C).

Figure 8. SEQ ID NO: 12 (9 amino acid linear CAR) and SEQ ID NOS: 20-23 (C A R S K N K D C, C-(D-allylglycine)-R-S-K-N-K-D-C, C A N S K N K D C, (N-meth)-C-A-R-S-K-N-K-D-C).

C-A-R-S-K-N-K-D-C
C-(D-allylglycine)-R-S-K-N-K-D-C
(N-meth)-C-A-R-S-K-N-K-D-C
C-A-N-S-K-N-K-D-C
C-A-R-S-k-N-K-D-C Figure 9. SEQ ID NO: 24 (7 amino acid linear CAR) and SEQ ID NOS: 25-28 (C A R S K N K, C-(D-allylglycine)-R-S-K-N-K, C A N S K N K, (N-meth)-C-A-R-S-K-N-K).

Sivelestat

CAR co-administered (500ug/mouse) every time when we administered drugs.

| Survival Rate (%) | | | | |
|---|---|---|---|---|
| | 12h | 24h | 36h | 48h |
| LPS only (n = 20) | 100 | 95 | 75 | 50 |
| Sivelestat 0.05mg/kg (n = 20) | 100 | 85 | 60 | 50 |
| Sivelestat 0.05mg/kg + CAR (n = 18) | 100 | 100 | 89 | 89 |

ATIII

CAR co-administered (500ug/mouse) every time when we administered drugs.

| Survival Rate (%) | | | | |
|---|---|---|---|---|
| | 12h | 24h | 36h | 48h |
| LPS only (n = 14) | 100 | 93 | 79 | 50 |
| ATIII 600U/kg (n = 10) | 100 | 80 | 40 | 40 |
| ATIII 300U/kg + CAR (n = 12) | 100 | 83 | 83 | 83 |

CAR co-administered (500μg/mouse) every time when we administered drugs.

| Survival Rate (%) | | | | |
|---|---|---|---|---|
| | 12h | 24h | 36h | 48h |
| LPS only (n = 14) | 100 | 100 | 79 | 50 |
| Steroid 0.5mg/kg (n = 16) | 100 | 94 | 56 | 56 |
| Steroid 0.5mg/kg + CAR (n = 18) | 100 | 100 | 83 | 83 |

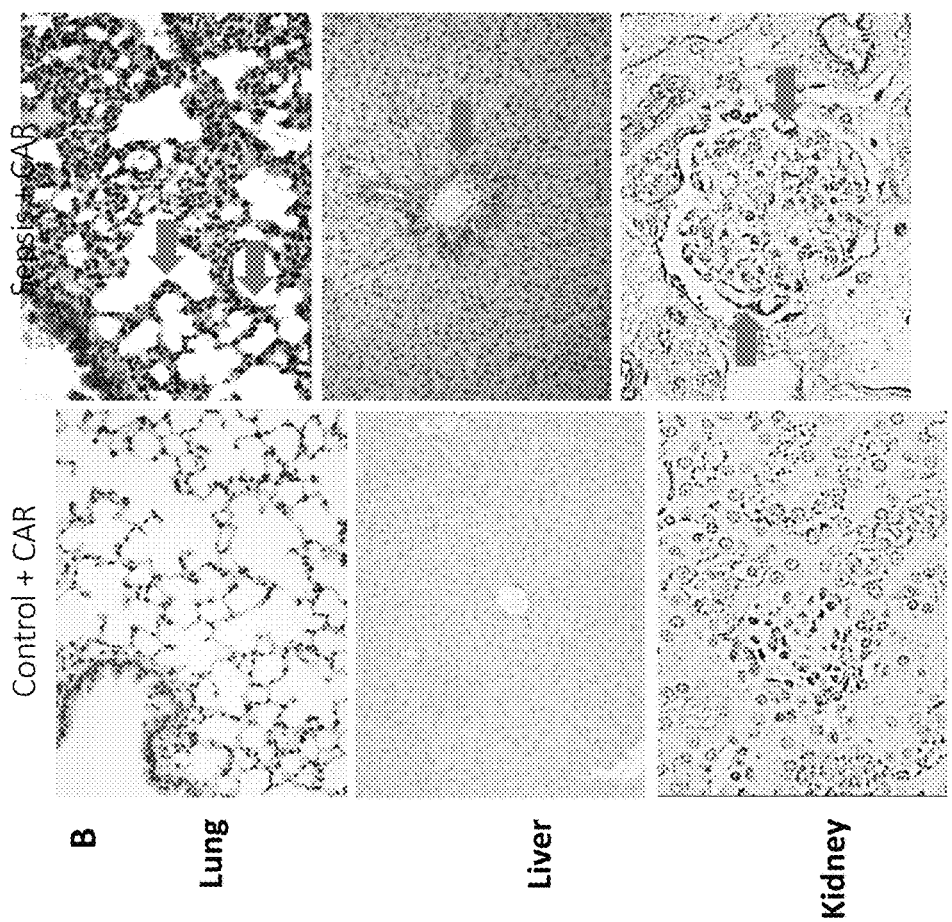
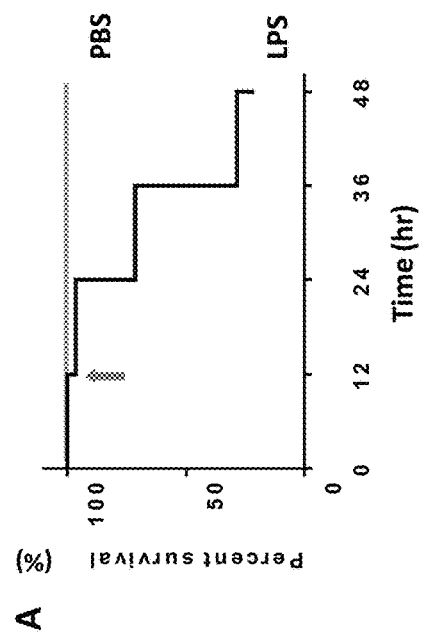
Figure 15.

| PASize(1m) | % Wall Thickness | | | | | |
|---|---|---|---|---|---|---|
| External diameter | Im50 | Im 50+CAR | % decrease | Im 10 | Im 10+CAR | % decrease |
| 25~50 | 59.96 | 54.09 | -9.79 | 63.30 | 57.29 | -9.50 |
| 50~100 | 44.61 | 42.52 | -4.69 | 58.24 | 52.38 | -10.05 |
| >100 | 50.52 | 39.09 | -22.63 | 56.26 | 53.97 | -4.07 |
| Total PA | 48.32 | 40.83 | -15.52 | 57.94 | 53.35 | -7.92 |

Figure 25. con't
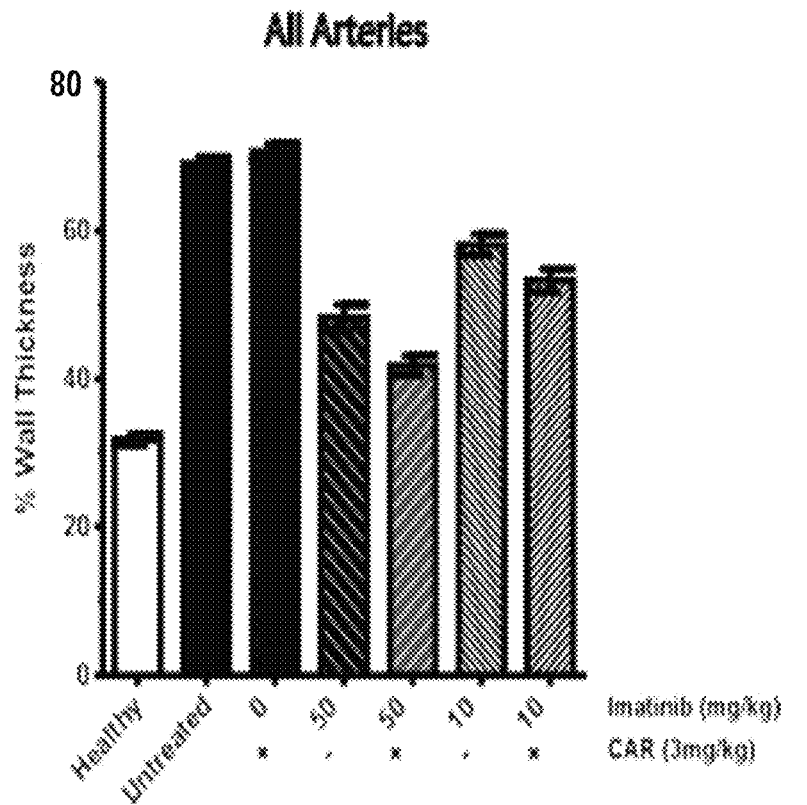
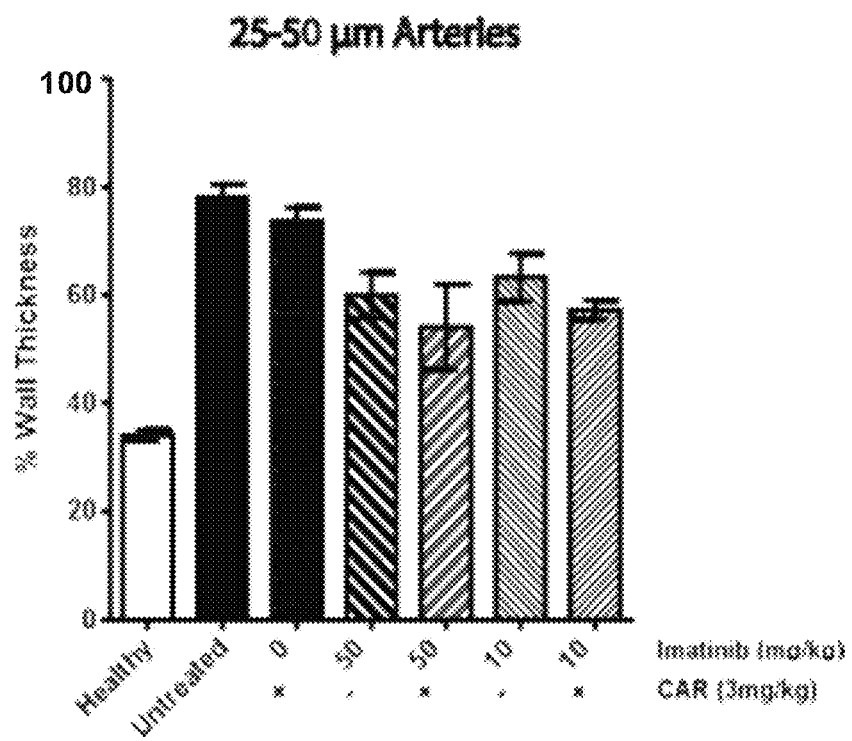

Figure 25. con't
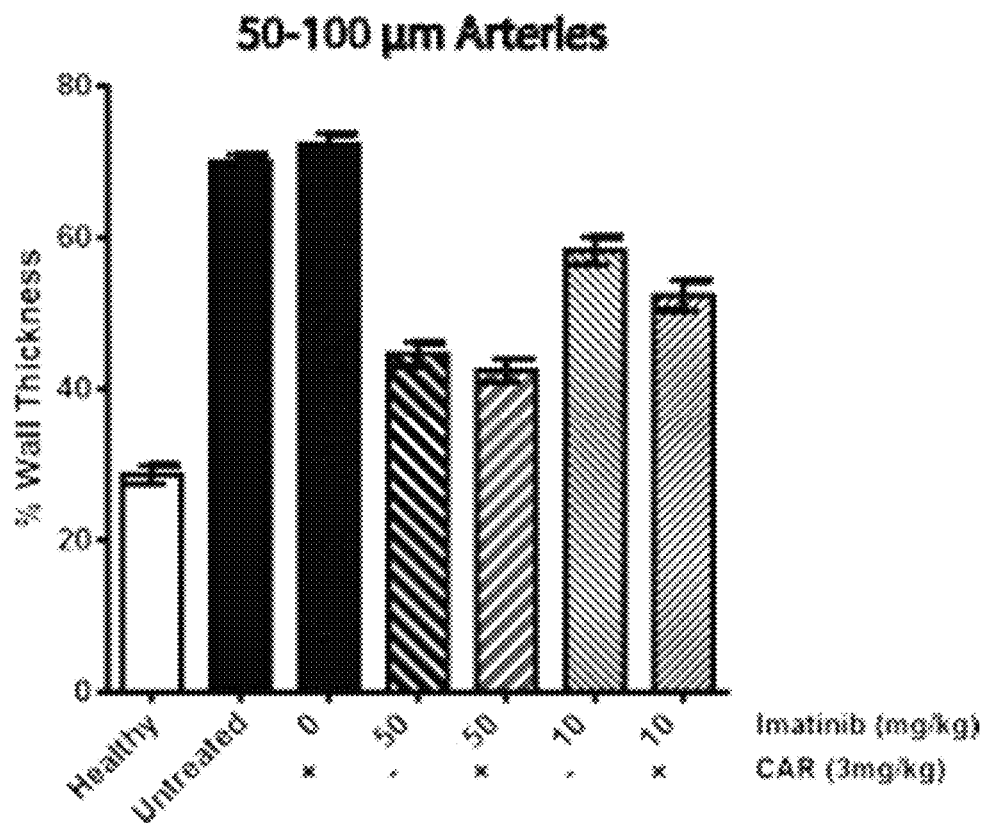
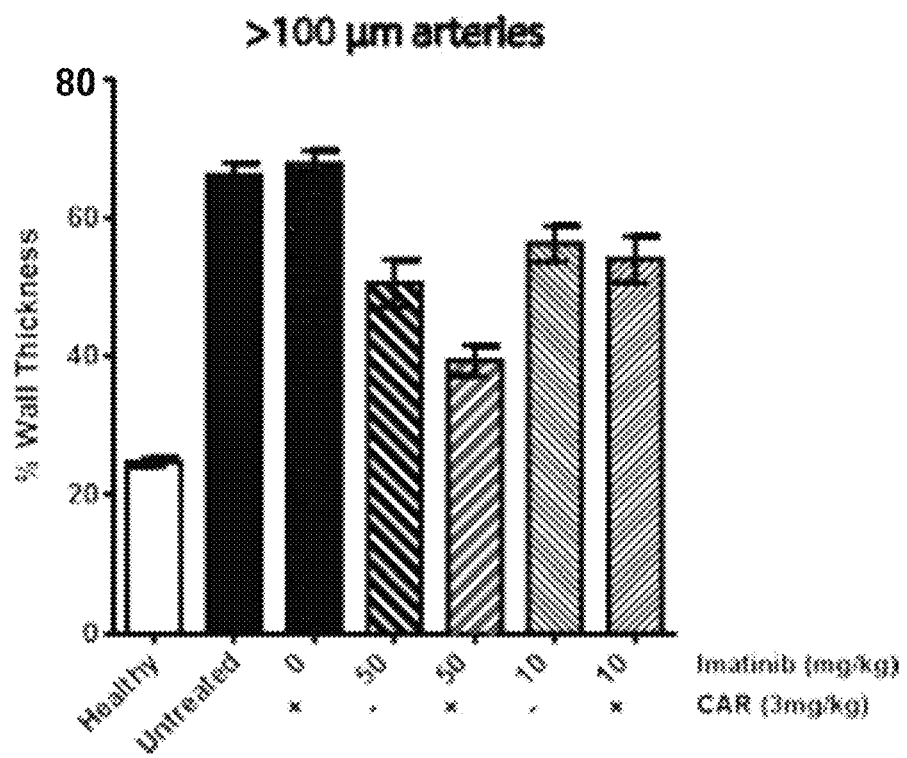

COMPOSITIONS CONTAINING A PHARMACOPHORE WITH SELECTIVITY TO DISEASED TISSUE AND METHODS OF MAKING SAME

RELATED APPLICATIONS

This application claims priority from International Patent Application No. PCT/US15/43686 filed Aug. 4, 2015 which claims priority from U.S. Provisional Application No. 62/034,046, filed on Aug. 6, 2014, and U.S. Provisional Application No. 62/161,121, filed on May 13, 2015, the contents of which are hereby incorporated by reference herein.

STATEMENT REGARDING FEDERALLY SPONSORED RESEARCH

This invention was made with government support under STTR grant No. R41 GM099174, and VITA contract No. HHSN268201400006C from the National Institute of Health (NIH).

FIELD OF THE INVENTION

This invention relates generally to the field of drug discovery and development, with specific attention given to molecules that selectively localize, bind, and internalize into diseased cells and tissue.

BACKGROUND OF THE INVENTION

A pharmacophore is defined as the conserved molecular features of a therapeutically active molecule that are necessary for the molecule to exert its biological activity. Structure-function relationship studies of a compound can provide valuable insight into the specific steric and electronic features required for optimal interactions between the compound and its specific biological target.

Identification of a pharmacophore can be useful for the design of structurally diverse molecules that possess similar biological activity. An understanding of the pharmacophore can lead to further details about the receptor-ligand interactions and other chemical and structural properties of an unknown receptor's active site. Proper identification of a pharmacophore would also allow for the potential optimization of compounds through the creation of analogues that have enhanced therapeutic selectivity or more desirable pharmacological properties.

A major hurdle in treating disease is the relative lack of agents that can selectively target the diseased tissue while sparing healthy tissue. There is a need for new therapeutic strategies for selectively targeting diseased tissue and reducing the side effects associated with systemic therapies. There is also a need for diagnostic agents that selectively identify diseased tissue. The identification of a pharmacophore that encompasses a class of molecules that possess disease selectivity and internalization properties would enable the development of compounds of significant therapeutic and diagnostic potential. The present invention satisfies this need by identifying a pharmacophore with selectivity for diseased tissue. The present invention also identifies molecules that fit this pharmacophore and can be useful for therapeutic or diagnostic purposes. These compounds are also suitable as stand alone therapeutics, as the homing moiety conjugated to a therapeutic or for selectively enhancing the effects of co-administered agents in diseased tissue.

Sepsis is a life-threatening medical condition caused by an intense immune response to infection. The natural chemicals released in the bloodstream to combat infection trigger system-wide inflammation, which can lead to multi-organ failure and death (National Institute of General Medical Sciences, 2014). Due to the nonspecific symptoms of sepsis that overlap with a multitude of other conditions and make sepsis difficult to diagnose, it has been estimated that the incidence of sepsis is severely underreported. Even so, it has been estimated that sepsis occurs in approximately 2% of all hospitalizations, and affects around 750,000 people a year in the United States alone (Martin 2012; Lever et al., 2007) The incidence of sepsis has also been rising, with the number of cases per year increasing from 164,072 in 1979 to 659,935 in 2000, and deaths for both respective years increasing from 43,579 to 120,491 (Lever et al., 2007). In addition, sepsis typically has high mortality rates, which vary from 10% in the mildest form, to close to 80% for patients with septic shock (Lever et al., 2007).

One drug therapy currently used in the treatment of sepsis is sivelestat, a neutrophil elastase inhibitor. However, the efficacy of sivelestat as a treatment for sepsis has not been convincingly demonstrated. One systematic review and meta-analysis examined 8 separate trials which used sivelestat, and found that sivelestat had no difference on the mortality rate within 28-30 days after randomization, no difference in the amount of mechanical ventilation days, and possibly increased the mortality rate for 180 day mortality (Iwata et al., 2010). The study concluded that sivelestat may be associated with improvement of oxygenation for a short period of time, and that the effect of sivelestat is modest, if there is any effect at all (Iwata et al., 2010)

Antithrombin III has also been used as a treatment for sepsis. Recent data suggests that in addition to its anticoagulant function, anti-thrombin is a potent anti-inflammatory agent, and studies have found that anti-thrombin III significantly reduced multi-organ failure and mortality in animal studies using lethal doses of *Escherichia coli* (Dept. Haematology, Royal Free University College London Medical School, 2001) With these results in mind, several clinical trials in patients with sepsis were run using an anti-thrombin therapy. Several of the smaller studies found that while anti-thrombin therapy did show a reduction in 30 day mortality, the difference was not statistically significant (Dept. Haematology, Royal Free University College London Medical School, 2001) The larger clinical trial found no survival difference between the group receiving anti-thrombin therapy and the placebo, but using subgroup analysis did find that anti-thrombin therapy showed a significant survival benefit in patients with septic shock, the most severe form of sepsis (Dept. Haematology, Royal Free University College London Medical School, 2001) One other randomized controlled trial tested high-dose anti-thrombin III in severe sepsis on a sample of over 2000 patients, and found that mortality was 38.9% in the anti-thrombin III group and 38.7% in the placebo group, and that secondary end points showed no difference between the two groups (Warren et al., 2001).

One final therapy that is frequently used to treat sepsis is steroid therapy. However, research has not found definitive results showing that steroid therapy helps sepsis, and in some cases, it has found that steroid treatment actually leads to secondary infections and has no effect on survival. In one study that tested low-dose hydrocortisone therapy for patients with septic shock, results showed that hydrocortisone did not improve survival in patients with septic shock, and there were more episodes of super infection in the hydrocortisone treatment group (Spring et al., 2008). Other studies testing hydrocortisone or other corticosteroids also found that there was no survival benefit, and the hydrocortisone or corticosteroid groups actually experienced more complications than the placebo groups (Rakela et al., 1991; Hotchkiss et al., 2003).

Despite intensive use of medical resources including hemodynamic support, fluid resuscitation, vasopressor therapy, augmented oxygen delivery, empiric antimicrobial therapy, and corticosteroid therapy, (Claessens et al., 2007; Kilal et al., 2014) the risk of death from sepsis ranges from 30-80% (Jawad et al., 2012). There is an urgent unmet need for innovative approaches that can improve sepsis survival.

CAR homes and exhibits preclinical efficacy in a wide range of injured, inflammatory and fibrotic disorders including wound healing (Jarvinen et al., 2007), pulmonary hypertension (Urakami et al., 2011; Toba et al., 2014), acute lung injury, pulmonary fibrosis, chronic kidney disease and triple-negative breast cancer induced cachexia (Mann et al., 2015). These seemingly disparate diseases share the common characteristic of an altered glycocalyx. Sepsis is also characterized by an altered glycocalyx (Chelazzi et al., 2015) making CAR a strong candidate for effectively reducing the mortality rate associated with sepsis through co-administration with existing drugs, as the homing moiety conjugated to a therapeutic, or through administering CAR alone as a therapeutic.

SUMMARY OF THE INVENTION

Disclosed herein are the features of the CAR pharmacophore essential for disease homing and internalizing properties, and further disclosed are molecular entities that fall within the scope of the CAR pharmacophore.

Disclosed herein are compounds containing the identified CAR pharmacophore. Disclosed are peptides that selectively target tumor vasculature, regenerating tissue, wounded tissue, inflamed tissue, fibrotic tissue, remodeled tissue, tissue characterized by elevated heparanase levels, and have the ability to internalize into such diseased cells. The disclosed compounds can also mediate the selective targeting, internalization, and tissue penetration of other conjugated, associated, or co-administered compounds.

Disclosed are compounds containing the cyclic, linear, or truncated CAR pharmacophore.

Also disclosed are any peptides or proteins containing an amino acid segment with the sequence of SEQ ID NOs: 1-8, 12, and 16-33, related amino acid sequences, or the CAR pharmacophore. The peptides or proteins can be comprised of an amino acid segment containing the amino acid sequence of SEQ ID NOs: 1-8, 12, and 16-33, or the amino acid sequence of SEQ ID NOs: 1-8, 12, and 16-33 having one or more conservative amino acid substitutions.

Also disclosed are any peptides or proteins containing an amino acid segment with the sequence of SEQ ID NOs: 1-8, 12, and 16-33, related amino acid sequences, or the CAR pharmacophore, where the amino acid sequence has undergone substitutional, insertional or deletional modifications. Disclosed are any conservative variants containing an amino acid segment with the sequence of SEQ ID NOs: 2-8, 12, and 16-33, related amino acid sequences, or the CAR pharmacophore. Also disclosed are conjugated compounds which possess the CAR pharmacophore, as well as compounds containing the CAR pharmacophore which have undergone chemical derivatization.

The disclosed compositions can be used with any molecular modeling, computational chemistry, or computer-aided drug design (CADD) technique to identify either the structure of SEQ ID NOs: 1-33 or to identify any other compounds containing the CAR pharmacophore. Disclosed are compounds containing the CAR pharmacophore that have been discovered or developed through the use of peptidomimetics.

Disclosed are molecules that have enhanced or desirable properties, such as, more economical production, greater chemical stability, reduced toxicity or side effects, enhanced pharmacological properties (e.g., half-life, absorption, distribution, metabolism, excretion, potency, efficacy, target binding or affinity, etc.), altered specificity (e.g., a broad-spectrum of biological activities), reduced antigenicity, and others. Also disclosed are molecules that have enhanced or desirable properties, such as, more economical production, greater chemical stability, reduced toxicity or side effects, enhanced pharmacological properties (e.g., half-life, absorption, distribution, metabolism, excretion, potency, efficacy, target binding or affinity, etc.), altered specificity (e.g., a broad-spectrum of biological activities), reduced antigenicity, and others.

Disclosed are bifunctional peptides which contain a homing peptide fused to a second peptide having a separate function. Also disclosed are the compositions that are identified through combinatorial techniques or screening techniques in which the compositions disclosed in SEQ ID NOs: 2-33 or portions thereof, are used as the target in a combinatorial or screening protocol.

Further disclosed are methods of identifying a cyclic CAR pharmacophore, the method comprising:
   a) performing permutations on the cyclic CAR peptide (SEQ ID NO:1) in order to synthesize at least seven additional, closely related peptides (SEQ ID NO:2-8);
   b) performing cell binding and internalization assays for SEQ ID NO:1-8;
   c) identifying any residues and sequence patterns from step b) which require conservation for CAR to retain biological activity;
   d) performing in silico modeling of SEQ ID NO:1-8 in order to create a small compound library and further identify the conserved molecular features of the CAR pharmacophore;
   e) superimposing the analogue models onto SEQ ID NO:1; and
   f) analyzing the superimposed analogues for conserved structural patterns.

Also disclosed are methods of identifying a pharmacophore of at least one therapeutically active molecule; the method comprising:
   a) performing permutations on the at least one therapeutically active molecule in order to synthesize analogues of the molecule;
   b) performing cell binding and internalization assays for the therapeutically active molecule and synthesized analogues;
   c) identifying any residues and sequence patterns from step b) which requires conservation for the molecule to retain therapeutic activity;
   d) performing in silico modeling of the therapeutically active molecule and analogues in order to create a small compound library and further identify the conserved molecular features of the pharmacophore;
   e) superimposing the analogue models onto the therapeutically active molecule model; and
   f) analyzing the superimposed analogues for conserved structural patterns.

In one embodiment the at least one therapeutic molecule which conveys a measurable therapeutic benefit to a disease may be selected from the group consisting of peptides that selectively target tumor vasculature, regenerating tissue, wounded tissue, inflamed tissue, fibrotic tissue, remodeled tissue, injured endothelium, tissue characterized by elevated heparanase levels, and have the ability to internalize into such diseased cells.

In another embodiment, the disease may be selected from the group consisting of pulmonary diseases, pulmonary hypertension, interstitial lung disease, acute lung injury, acute respiratory distress syndrome, asthma, sepsis, septic shock, infection, sarcoidosis of the lung, pulmonary manifestations of connective tissue diseases, including systemic lupus erythematosus, rheumatoid arthritis, scleroderma, and polymyositis, dennatomyositis, bronchiectasis, asbestosis, berylliosis, silicosis, Histiocytosis X, pneumonia, pneumonitis, smoker's lung, bronchiolitis obliterans, pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, scar formation, keloid, arthrofibrosis, adhesive capsulitis, radiation fibrosis, fibrocystic breast condition, liver cirrhosis, hepatitis, liver fibrosis, nonalcoholic fatty liver disease, acute liver failure, nonalcoholic steatohepatitis, sarcoidosis of the lymph nodes, or other organs; inflammatory bowel disease, Crohn's disease, cachexia, chronic kidney disease, acute kidney injury, acute renal failure, polycystic kidney disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, angiogenic diseases, wound healing, infections, trauma injuries and systemic connective tissue diseases including systemic lupus erythematosus, rheumatoid arthritis scleroderma, polymyositis, dermatomyositis, cystic fibrosis, erectile dysfunction, α1-antitrypsin deficiency, diabetes, diseases characterized by high heparanase levels, neuroinflammatory conditions, stroke, CNS degenerative diseases, such as Alzheimer's Disease, Parkinson's disease (PD), Huntington's disease, amyotrophic lateral sclerosis, multiple sclerosis, traumatic brain injury, hypoxia, aging brain, wet macular degeneration, neovascular age-related macular degeneration, diabetic retinopathy, glioblastoma, and senescence-related diseases.

In a preferred embodiment, the disease may be selected from the group consisting of pulmonary arterial hypertension, sepsis, kidney disease, cancer and cachexia.

Also disclosed are methods of treating an individual suffering from a disease, the method comprising:
 a) providing a targeting peptide comprising a sequence substantially identical to a CAR pharmacophore, the sequence selected from the group consisting of SEQ ID NO:16-SEQ ID NO:33, or a variant thereof;
 (b) providing at least one therapeutic molecule which conveys a measureable therapeutic benefit to a disease selected from the group consisting of pulmonary diseases, pulmonary hypertension, interstitial lung disease, acute lung injury, acute respiratory distress syndrome, asthma, sepsis, septic shock, infection, sarcoidosis of the lung, pulmonary manifestations of connective tissue diseases, including systemic lupus erythematosus, rheumatoid arthritis, scleroderma, and polymyositis, dennatomyositis, bronchiectasis, asbestosis, berylliosis, silicosis, Histiocytosis X, pneumonia, pneumonitis, smoker's lung, bronchiolitis obliterans, pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, scar formation, keloid, arthrofibrosis, adhesive capsulitis, radiation fibrosis, fibrocystic breast condition, liver cirrhosis, hepatitis, liver fibrosis, nonalcoholic fatty liver disease, acute liver failure, nonalcoholic steatohepatitis, sarcoidosis of the lymph nodes, or other organs; inflammatory bowel disease, Crohn's disease, cachexia, chronic kidney disease, acute kidney injury, acute renal failure, polycystic kidney disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, angiogenic diseases, wound healing, infections, trauma injuries and systemic connective tissue diseases including systemic lupus erythematosus, rheumatoid arthritis scleroderma, polymyositis, dermatomyositis, cystic fibrosis, erectile dysfunction, α1-antitrypsin deficiency, diabetes, diseases characterized by high heparanase levels, neuroinflammatory conditions, stroke, CNS degenerative diseases, such as Alzheimer's Disease, Parkinson's disease (PD), Huntington's disease, amyotrophic lateral sclerosis, multiple sclerosis, traumatic brain injury, hypoxia, aging brain, wet macular degeneration, neovascular age-related macular degeneration, diabetic retinopathy, glioblastoma, and senescence-related diseases;
 c) co-administering a composition comprising a) and b) to an individual in need thereof; and
 d) measuring a therapeutic benefit to the individual.

Further disclosed are methods of treating an individual suffering from a disease, the method comprising:
 a) providing a targeting peptide comprising a sequence substantially identical to a CAR pharmacophore, the sequence selected from the group consisting of SEQ ID NO:16-SEQ ID NO:33, or a variant thereof;
 (b) providing at least one therapeutic molecule which conveys a measureable therapeutic benefit to a disease selected from the group consisting of pulmonary arterial hypertension (PAH), sepsis and cachexia;
 c) co-administering a composition comprising a) and b) to an individual in need thereof; and
 d) measuring a therapeutic benefit to the individual.

In one embodiment, the at least one therapeutic molecule may be selected from the group consisting of imatinib, sivelestat, paclitaxel, antithrombin III, hydrocortisone.

Also disclosed are methods of treating an individual suffering from a disease, the method comprising:
 a) providing a targeting peptide comprising a sequence substantially identical to a CAR pharmacophore, the sequence selected from the group consisting of SEQ ID NO:16-SEQ ID NO:33, or a variant thereof;
 b) administering the targeting peptide in a) wherein the peptide conveys a measurable therapeutic benefit to a disease selected from the group consisting of pulmonary diseases, pulmonary hypertension, interstitial lung disease, acute lung injury, acute respiratory distress syndrome, asthma, sepsis, septic shock, infection, sarcoidosis of the lung, pulmonary manifestations of connective tissue diseases, including systemic lupus erythematosus, rheumatoid arthritis, scleroderma, and polymyositis, dennatomyositis, bronchiectasis, asbestosis, berylliosis, silicosis, Histiocytosis X, pneumonia, pneumonitis, smoker's lung, bronchiolitis obliterans, pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, scar formation, keloid, arthrofibrosis, adhesive capsulitis, radiation fibrosis, fibrocystic breast condition, liver cirrhosis, hepatitis, liver fibrosis, nonalcoholic fatty liver disease, acute liver failure, nonalcoholic steatohepatitis, sarcoidosis of the lymph nodes, or other organs; inflammatory bowel disease, Crohn's disease, cachexia, chronic kidney disease, acute kidney injury, acute renal failure, polycystic kidney disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, angiogenic diseases, wound healing, infections, trauma injuries and systemic connective tissue diseases including systemic lupus erythematosus, rheumatoid arthritis scleroderma, polymyositis, dermatomyositis, cystic fibrosis, erectile dysfunction, α1-antitrypsin deficiency, diabetes, diseases characterized by high heparanase levels, neuroinflammatory conditions, stroke, CNS degenerative diseases, such as Alzheimer's Disease, Parkinson's disease (PD), Huntington's disease, amyotrophic lateral sclerosis, multiple sclerosis, traumatic brain injury, hypoxia, aging brain, wet macular degeneration, neovascular age-related macular degeneration, diabetic retinopathy, glioblastoma, and senescence-related diseases, and c) measuring a therapeutic benefit to the individual.

In a preferred embodiment, the disease may be selected from the group consisting of PAH, sepsis, cancer and cachexia.

Also disclosed herein are conjugates, wherein the conjugate comprises a moiety linked to a peptide as disclosed herein. The moiety can be an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, gadolinium, iron oxide, iodine containing contrast medium, barium sulfate, gallium, 18F-fluorodeoxyglucose, Cuprymina, 3'-deoxy-3'-[18F]fluorothymidine, indium-111, technetium-99, carbon-11, carbon-13, or a combination. The moiety can be a therapeutic, agent, a detectable agent, a virus, or a phage. Disclosed are conjugates, wherein the conjugate comprises a moiety linked to a peptide comprising an amino acid segment comprising, for example, the amino acid sequence of SEQ ID NO: 1 to SEQ ID NO: 33.

Disclosed are conjugates comprising a moiety and a homing molecule, such as a peptide as disclosed herein. For example, disclosed are conjugates containing a therapeutic agent linked to a homing molecule that selectively homes to regenerating tissue, wound tissue, or tumors. Disclosed conjugates can comprise, for example, a moiety linked to a peptide comprising an amino acid segment comprising, for example, the amino acid sequence of SEQ ID NO: 1 to SEQ ID NO: 33.

Any form or type of homing molecule as disclosed herein can be used in the disclosed conjugates. The moiety can be any molecule. Preferably the moiety is a molecule that is usefully targeted to the target of the homing molecule. For example, moieties that affect the target, such as moieties with therapeutic effect, or that facilitate detection, visualization or imaging of the target, such as fluorescent molecules, radiocontrast agents, or radionuclides. Disclosed peptides that home to regenerating tissue, wound tissue, or tumors can be usefully combined with, for example, moieties that can, for example, promote wound healing, treat inflammation or pain, or treat cancer. A variety of therapeutic agents are useful in the conjugates including, without limitation, a moiety that is an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, gadolinium, iron oxide, iodine containing contrast medium, barium sulfate, gallium, 18F-fluorodeoxyglucose, Cuprymina, 3'-deoxy-3'-[18F]fluorothymidine, indium-111, technetium-99, carbon-11, carbon-13, or a combination.

A conjugate can contain, for example, a liposome or other polymeric matrix linked to at least two homing molecules. If desired, the liposome or other polymeric matrix can be linked to at least ten, at least 100 or at least 1000 homing molecules. Liposomes can be useful in such conjugates; liposomes consist of phospholipids or other lipids, are nontoxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, diagnostic agent, anti-angiogenic agent, polypeptide or nucleic acid molecule.

In some embodiments, a conjugate can contains a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

The conjugates can be used to treat or diagnose any disease, condition, or disorder disclosed herein, for example, pulmonary arterial hypertension, sepsis, cancer and cachexia.

The compositions can be administered orally (e.g., sublingually), parenterally (e.g.; intravenously), by intramuscular injection, by intraperitoneal injection, transdermally, extracorporeally, topically or the like, including topical intranasal administration or administration by inhalation. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via inhalation or intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Also disclosed herein are methods of directing a moiety to regenerating tissue, comprising administering to a subject a conjugate, as disclosed herein. Disclosed are methods wherein the therapeutic effect comprises a reduction in inflammation, an increase in speed of wound healing, a reduction in the amount of scar tissue, decrease in pain, decrease in swelling, decrease in infection, or decrease in necrosis.

Also disclosed are methods of directing a moiety to tumors, comprising administering to a subject a conjugate as disclosed herein. The conjugate can have a therapeutic effect, and the subject can have one or more sites to be targeted, wherein the moiety is directed to one or more of the sites to be targeted. The subject can have cancer, wherein the moiety is directed to tumor angiogenesis in the subject. The conjugate can have a therapeutic effect on the cancer, such as reducing the size or growth of a tumor. The moiety can also be used to detect the cancer, visualize one or more tumors, or both.

In one embodiment, the variant may be of the formula CxRxRxR, wherein R is selected from the group consisting of K or R, and further wherein X is selected from the group consisting of T, S, N, Q, A, I, L or V.

In yet another embodiment, the present invention provides an isolated polypeptide comprising an amino acid sequence at least about 90% identical to at least one member selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8.

BRIEF DESCRIPTION OF THE DRAWINGS

The accompanying drawings illustrate several embodiments of the disclosed method and compositions and together with the description, and serve to explain the principles applied to the respective method and/or composition.

FIG. 1. Cyclic peptides tested to determine cyclic CAR pharmacophore.

FIG. 4. Superimpositions of all 8 variants tested (SEQ ID NOs: 1-8), including original cCAR. This figure superimposes SEQ ID NOs: 1-8 to illustrate the conserved features of the CAR pharmacophore.

FIG. 5. Cyclic CAR (SEQ ID NO:1), along with CAR-Rifabutin, CAR-Rapamycin, and CAR-Voclosporin analogues (SEQ ID NOs: 9-11). These compounds have been structurally modified from existing macrocycles to produce compounds containing the CAR pharmacophore and would possess similar homing and internalization properties as SEQ ID NO: 1.

FIG. 6. Linear 9 amino acid CAR (SEQ ID NO: 12), along with linear CAR-Rifabutin, linear CAR-Rapamycin, and linear CAR-Voclosporin analogues (SEQ ID NOs: 13-15). The structural modifications shown here once again illustrate certain modifications that could be made to existing molecules to produce compounds containing the CAR pharmacophore.

FIG. 7. Superimposition of cCAR and unnatural cCAR analogues (SEQ ID NOs:1 and 16-19). Substitutions at various positions include: 1) D-amino acid; 2) D-allylglycine; 3) Diamino acid (Asn substitution at Arg position); 4) N-methyl amino acid. Once again, these compounds have been structurally modified, in an attempt to illustrate modifications that one would perform on CAR peptide to produce a "new" compound with nearly identical properties as CAR.

FIG. 8. Superimposition of 9 amino acid linear CAR (SEQ ID NO: 12) along with 9 amino acid linear CAR analogues (unnatural substitutions; SEQ ID NOs: 20-23). Substitutions at various positions include: 1) D-amino acid; 2) D-allylglycine; 3) Diamino acid (Asn substitution at Arg position); 4) N-methyl amino acid.

FIG. 9. Superimposition of 7 amino acid linear CAR (SEQ ID NO: 24) along with unnatural linear 7 amino acid CAR analogues (SEQ ID NOs: 25-28). Substitutions at various positions include: 1) D-amino acid; 2) D-allylglycine; 3) Diamino acid (Asn substitution at Arg position); 4) N-methyl amino acid. Original linear 7 amino acid CAR is represented in the larger "sticks" rendering, while all variants are shown in a "lines" rendering.

FIG. 10. CAR targeting of crescentic glomerula nephritis. Masson's trichome staining (A). Fibronectin immunostaining (B). CAR accumulation (C). Control accumulation (D).

FIG. 11. Hypothesized mechanism of CAR pharmacophore action in sepsis.

FIG. 12. Effect of addition of CAR pharmacophore to sivelestat in LPS induced sepsis mice.

FIG. 13. Effect of addition of CAR pharmacophore to ATIII in LPS induced sepsis mice.

FIG. 14. Effect of addition of CAR pharmacophore to hydrocortisone in LPS induced sepsis mice.

FIG. 15. A) Survival of LPS induced sepsis mice; B) Histology of lung, liver and kidney tissue from LPS induced sepsis mice.

FIG. 16. Localization of CAR pharmacophore in kidney tissue from LPS induced sepsis mice.

FIG. 17. Scanning electron micrograph of lung tissue from control, sivelestat and CAR pharmacophore+sivelestat treated mice.

FIG. 18. Scanning electron micrograph of liver tissue from control, sivelestat and CAR pharmacophore+sivelstat treated mice.

FIG. 19. Scanning electron micrograph of kidney tissue from control, sivelestat and CAR+sivelestat treated mice.

FIG. 20. Effect of CAR pharmacophore on Acute Kidney Injury Marker (KIM-1).

FIG. 21. Effect of CAR pharmacophore on cancer associated cachexia in triple negative breast cancer mice.

FIG. 22. Effect of CAR pharmacophore adjuvant on right heart hypertrophy.

FIG. 23. Effect of CAR pharmacophore adjuvant on bodyweight in PAH model rats.

FIG. 24. Effect of oral CAR pharmacophore on right heart hypertrophy.

DETAILED DESCRIPTION OF THE INVENTION

Definitions

Figure 2:
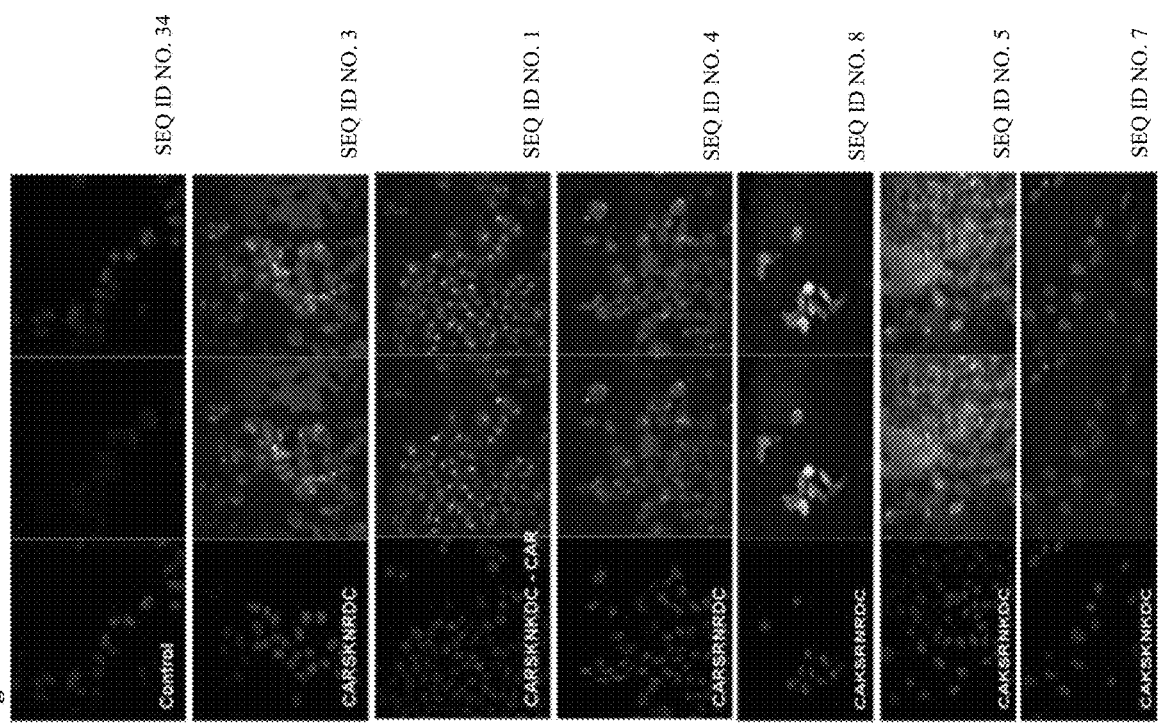
FIG. 2. Binding and internalization of CAR peptide variants into CHO-K cells. FAM-conjugated peptides as indicated were incubated at 5 µM concentration with CHO-K cells for 2 hours. The cells were washed, fixed, stained with the nuclear stain DAPI. Original magnification ×400.

The term "CAR pharmacophore," as used herein, is defined as the conserved molecular features of cyclic (SEQ ID NO: 1), linear (SEQ ID NO: 12), and truncated (SEQ ID NO: 24) CAR peptides, that are necessary for CAR's disease homing, target binding, internalization, and biological activity. We herein refer to the truncated, linear, and cyclic CAR pharmacophores collectively as the "CAR pharmacophore."

As used herein, the term "peptide" is used broadly to mean peptides, proteins, fragments of proteins and the like. The term "peptidomimetic," as used herein, means a peptide-like molecule that has the activity of the peptide upon which it is structurally based.

I. General

Recent studies (Jarvinen 2007; Urakami 2011; Jarvinen 2010; Toba 2014; US Patent App. Pub. No: 2009/0036349 A1) have identified a disease homing and cell penetrating peptide with sequence CARSKNKDC (CAR; SEQ ID NO: 1). Additional experimental studies have determined that linear CAR (SEQ ID NO: 12) and truncated CAR (tCAR; SEQ ID NO: 24) also possess similar biological activity (US Patent App. Pub. No: 2012/0034164 A1). Despite our knowledge of CAR's biological activity, its precise receptor remains unknown. Identification of CAR's pharmacophore would be invaluable in exploring CAR's receptor, elucidating its mechanism of action (MOA), and designing other potentially more useful compounds.

In an attempt to identify the cyclic CAR pharmacophore, cell binding and internalization assays for cyclic CAR peptide (SEQ ID NO: 1) and seven closely related peptides (SEQ ID NOs: 2-8) were performed. In addition to cyclic CAR (SEQ ID NO: 1), seven other cyclic peptides were synthesized (SEQ ID NOs: 2-8) containing permutations on either the Lys or Arg residues, and were labeled by attaching a fluorescamine (FAM) group to the molecule (FIG. 1). A cell binding and internalization assay was used as an initial test to compare the permutated compounds to the original CAR peptide. Cell binding and internalization of the peptides was studied using confocal microscopy and Chinese Hamster Ovary (CHO-K) cells, which have been previously used to study CAR binding. Fluorescence-activated cell sorting (FACS) was also used to determine cell internalization of SEQ ID NOs: 1-8. The cell binding and internalization assays identified certain features of the CAR pharmacophore in terms of conserved residue and sequence patterns that need to be conserved in order for the compound to retain its biological activity.

In order to further identify the conserved molecular features of the CAR pharmacophore, SEQ ID NOs: 1-8 were produced in silico using computational modeling techniques. A variety of renderings were displayed in order to compare/contrast the various molecular features of SEQ ID NOs: 1-8. Analysis of the superimposed CAR analogues (FIG. 4) revealed a conserved cyclic CAR structural pattern that has been identified as the cyclic CAR pharmacophore. This is due to the striking structural, electronic, steric, and sequential similarities of SEQ ID NOs: 1-8.

The in silico modeling served to further define the previously identified CAR pharmacophore, which can not only be defined in terms of precise sequences and residue patterns, but can also be defined in terms of more generalized structures that possess similar three-dimensional, spatial, and electronic patterns as the linear, truncated, and cyclic CAR peptides. These results confirm the data generated in the cell binding and internalization assays, where SEQ ID NOs: 2-8 display similar biological activity to SEQ ID NO: 1. As a result, it was concluded that SEQ ID NOs: 2-8 would possess similar therapeutic activity to the original CAR sequence (SEQ ID NO: 1), and that all sequences fall within the CAR pharmacophore.

Based on experimental studies and the results of computational modeling the CAR pharmacophore has been determined. In analyzing these molecules, conserved features that are necessary for their respective biological activity have been identified. Furthermore, since tCAR possesses similar properties as cCAR, the identity of a linear and truncated CAR pharmacophore (in addition to the cyclic CAR pharmacophore) can be deduced. This provides further evidence that, although linearized, the conserved features of the CAR pharmacophore can still be present in linear and truncated variants, and can still retain the properties of the original cyclic CAR peptide.

Following identification of the cyclic, linear, and truncated CAR pharmacophores (collectively referred to as the CAR pharmacophore), additional structures that retain these essential molecular features were generated. Utilizing molecular modeling/computational chemistry, peptidomimetics, sequence variation techniques, and computer assisted drug design, library of compounds (SEQ ID NOs: 9-33) was produced that have been specifically designed to contain the CAR pharmacophore, which is required for disease homing and selective internalization. These structures were produced to illustrate the wide variety of novel compounds that could be generated that possess the CAR pharmacophore, along with CAR peptide's disease homing and internalization properties.

II. Materials

A. Peptides and Proteins

Disclosed are any peptides or proteins containing an amino acid segment with the sequence of SEQ ID NOs: 1-8, 12, and 16-33, related amino acid sequences, or the CAR pharmacophore. The peptides or proteins can be comprised of an amino acid segment containing the amino acid sequence of SEQ ID NOs: 1-8, 12, and 16-33, or the amino acid sequence of SEQ ID NOs: 1-8, 12, and 16-33 having one or more conservative amino acid substitutions. The amino acid segment can be composed of an amino acid sequence that is 60%, 70%, 80%, 90%, or 100% identical to the amino acid sequence of SEQ ID NOs: 1-8, 12, and 16-33, or any percentage in between that represents a change, including addition, deletion, or substitution, of one or more amino acid residues. The amino acid segment can comprise the amino acid sequence of SEQ ID NOs: 1-8, 12, and 16-33 having one, two, three, four, five, six, seven, eight, or nine conservative amino acid substitutions. The amino acid segment can comprise a chimera of the amino acid sequence SEQ ID NOs: 1-8, 12, and 16-33. Such a chimera can be additive, where sequence of one sequence is added to another sequence, substitutional, where sequence of one sequence is substituted for sequence of another sequence, or a combination.

Also disclosed are amino acid segments containing the CAR pharmacophore, wherein the segments can be linear (including truncated linear peptides), circular or cyclic. The amino acid segment can be circularized or cyclized via any suitable linkage, for example, a disulfide bond or peptide bond. The peptide can have any length.

Also disclosed are peptides or proteins containing the CAR pharmacophore which can selectively home to regenerating tissue, wound tissue, or tumors. The disclosed peptides can selectively interact with regenerating tissue, wound tissue, or tumors.

Also disclosed are isolated peptides or proteins which have a length of less than 100 residues and which include the amino acid sequence of SEQ ID NOs: 1-8, 12, and 16-33 or the CAR pharmacophore. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides and proteins containing an amino acid segment with the sequence of SEQ ID NOs: 1-8, 12, and 16-33, related amino acid sequences, or the CAR pharmacophore, can have any suitable length.

B. Computational Modeling

The disclosed compositions can be used with any molecular modeling, computational chemistry, or computer-aided drug design (CADD) technique to identify either the structure of SEQ ID NOs: 1-33 or to identify any other compounds containing the CAR pharmacophore. It is understood that when using the disclosed compositions (SEQ ID NOs: 1-33) in modeling techniques, compounds will be identified that have particular desirable properties such as selective homing to sites of disease and cellular internalization at the site of disease.

Also disclosed are compounds containing the CAR pharmacophore that have been discovered through the use of rational design. This can be achieved using structural information and/or computer modeling. Computer modeling technology allows visualization of the three-dimensional atomic structure of a selected molecule, and the knowledge of this three-dimensional atomic structure can allow for determination and optimal placement of chemical functional groups in the rational design of new compounds. The three-dimensional construct can be obtained from x-ray crystallographic analyses or NMR imaging of the molecule containing the CAR pharmacophore. The use of molecular dynamics and force field data could also be used in the discovery of compounds containing the CAR pharmacophore. Computer graphics systems can enable prediction of how a compound will bind to its respective receptor, and experimental manipulation of the compound structure/sequence can be performed to optimize binding specificity. The virtual screening of compound libraries, including synthetic chemicals, peptides, proteins, and other biologically active materials, can also be performed to discover novel compounds containing the CAR pharmacophore.

C. Peptidomimetics

Also disclosed are compounds containing the CAR pharmacophore that have been discovered or developed through the use of peptidomimetics. Peptidomimetics include chemically modified peptides, peptide-like molecules containing non-naturally occurring amino acids, as well as proteins. Peptidomimetic compounds may possess selective disease homing activity and/or target cell internalization abilities such as SEQ ID NO: 1.

Also disclosed are isolated multivalent peptides that include at least two subsequences each independently containing a homing molecule (for example, the amino acid sequences SEQ ID NOs: 2-33, or a conservative variant or peptidomimetic thereof). The multivalent peptide can have, for example, at least three, at least five or at least ten of such subsequences each independently containing a homing molecule (for example, the amino acid sequence of SEQ ID NOs: 2-33, or a conservative variant or peptidomimetic thereof). In particular embodiments, the multivalent peptide can have two, three, four, five, six, seven, eight, nine, ten, fifteen or twenty identical or non-identical subsequences. In a further embodiment, the multivalent peptide can contain identical subsequences, which consist of a homing molecule (for example, the amino acid sequence SEQ ID NOs: 2-33, or a conservative variant or peptidomimetic thereof). In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

A variety of peptidomimetics are known, including peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^{\alpha}$—$C^{\alpha}$ cyclized amino acid; an $N^{\alpha}$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^{\varepsilon}$ or $C^{\alpha}$-$C^{\Delta}$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere.

Also disclosed are methods for identifying a peptidomimetics containing the CAR pharmacophore, and can include, for example, the screening of databases that contain libraries of potential CAR pharmacophore peptidomimetics. As an example, the Cambridge Structural Database contains a collection of greater than 300,000 compounds that have known crystal structures (Allen et al., Acta Crystalloqr. SectionB, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chern. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively homing to tumor stroma, wounds, and plasma clots.

D. Substitutional Variants Also disclosed are any peptides or proteins containing an amino acid segment with the sequence of SEQ ID NOs: 1-8, 12, and 16-33, related amino acid sequences, or the CAR pharmacophore, where the amino acid sequence has undergone substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein or peptide sequence. Typically, no more than about 2 to 6 residues are deleted at anyone site within the protein or peptide molecule. These variants can be prepared by site specific mutagenesis of nucleotides in the DNA encoding the protein or peptide, thereby producing DNA encoding the variant, and thereafter expressing the DNA in recombinant cell culture. Substitutional, insertional or deletional modifications can include, but are not limited to, unnatural amino acids, D-amino acids, or any other residue(s) that may result in generation of altered or improved compound(s) that still possess the CAR pharmacophore.

Techniques for making substitution mutations at predetermined sites in DNA having a known sequence are well known. Amino acid substitutions are typically of single residues, but can occur at a number of different locations at once; insertions usually will be on the order of about from 1 to 10 amino acid residues; and deletions will range about from 1 to 10 residues. Deletions or insertions preferably are made in adjacent pairs, i.e. a deletion of 2 residues or insertion of 2 residues. Substitutions, deletions, insertions or any combination thereof can be combined to arrive at a final construct containing the CAR pharmacophore. Substitutional variants are those in which at least one residue has been removed and a different residue inserted in its place.

E. Conserved Variants

Also disclosed are any conservative variants containing an amino acid segment with the sequence of SEQ ID NOs: 1-8, 12, and 16-33, related amino acid sequences, or the CAR pharmacophore. A conservative variant is a sequence in which a first amino acid is replaced by another amino acid or amino acid analog having at least one biochemical property similar to that of the first amino acid; similar properties include, for example, similar size, charge, hydrophobicity or hydrogen bonding capacity. A conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of SEQ ID NOs: 1-8, 12, and 16-33 encompass sequences containing one, two, three, four or more amino acid substitutions relative to SEQ ID NOs: 1-8, 12, and 16-33, and that such variants can include naturally and non-naturally occurring amino acid analogs.

Also disclosed are compounds containing the CAR pharmacophore in which less conservative amino acid substitutions have been made. This can include selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, for example, phenylalanine, is substituted for (or by) one not having a side chain, e.g., glycine, in this case, (e) by increasing the number of sites for sulfation and/or glycosylation.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, are accomplished for example by deleting one of the basic residues or substituting one by glutaminyl or histidyl residues.

F. Derivatizations

Derivitization is a process by which a compound is modified into a product of similar chemical structure. Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86; 1983), acetylation of the N-terminal amine and, in some instances, amidation of the C-terminal carboxyl.

It is understood that one way to define the variants and derivatives of the disclosed proteins herein is through defining the variants and derivatives in terms of homology/ identity to specific known sequences. Specifically disclosed are variants of these and other proteins herein disclosed which have at least, 70% or 75% or 80% or 85% or 90% or 95% homology to the stated sequence, or any percentage in between that represents a change of amino acid, including a substitution, addition, or deletion. Those of skill in the art readily understand how to determine the homology of two proteins. For example, the homology can be calculated after aligning the two sequences so that the homology is at its highest level.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D-amino acids or amino acids which have a different functional substituent than those discussed above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., MS, 14(10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

Also disclosed are molecules which can be produced that resemble peptides, but which are not connected via a natural peptide linkage. For example, linkages for amino acids or amino acid analogs can include: $CH_2NH$—, —$CH_2S$—, —$CH_2$—$CH_2$—, —CH═CH-(cis and trans), —$COCH_2$—, —CH(OH)$CH_2$—, and —CHH$_2$SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CHH$_2$—S); Harm J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

G. Conjugates

Also disclosed are conjugated compounds which possess the CAR pharmacophore. The conjugate could be a linear or cyclic variant of the CAR pharmacophore, and can be linked to another compound using disulfide bonds, peptide bonds, or any other type of covalent or non-covalent chemical modification resulting in the linking the CAR pharmacophore variant to one or more other compounds, or linking a linear or cyclic variant of the CAR pharmacophore to a liposome, nanoerythrosome or micelle containing a therapeutic or diagnostic payload. In one embodiment, truncated CAR (tCAR; SEQ ID NO: 24) has been conjugated to free sulfhydryl group at the Cys34 residue of human serum albumin (HSA) via a disulfide bond (Sugio 1999). This HSA-tCAR conjugate could prolong the half-life of tCAR (Dennis 2002), and is illustrative of a much broader approach that can be used to enhance the properties, such as half-life, of a CAR pharmacophore variant.

In another embodiment, the CAR pharmacophore could be linked to an anti-fibrotic compound such as decorin to produce targeted fibrotic inhibition such as in scar reduction.

This idea of conjugation of a molecule containing the CAR pharmacophore to another molecule can have the effect of extending half-life, improving the affinity to diseased tissue, improving toxicity or pharmacokinetic properties, improved selectivity, improved binding and/or internalization, or improving the therapeutic effects of either of the conjugated compounds. In another embodiment, cyclic CAR (SEQ ID NO: 1) has been covalently linked (via a peptide bond) to the Fv fragment of the monoclonal anti-cancer antibody B1. This antibody has an affinity for human carcinoma cells. This could result in a drug conjugate with a high degree of specificity to human cancer cells, and is illustrative of a broader class of compounds containing the CAR pharmacophore that would have improved disease homing properties.

H. Optimized Compounds

Also disclosed are amino acid and peptide analogs that have enhanced or desirable properties, such as, more economical production, greater chemical stability, reduced toxicity or side effects, enhanced pharmacological properties (e.g., half-life, absorption, distribution, metabolism, excretion, potency, efficacy, target binding or affinity, etc.), altered specificity (e.g., a broad-spectrum of biological activities), reduced antigenicity, and others. In one embodiment, D-amino acids can be used to generate more stable peptides, because D-amino acids are not recognized by peptidases. Systematic substitution of one or more amino acids of a consensus sequence with a D-amino acid of the same type (e.g., D-lysine in place of L-lysine) can be used to generate more stable peptides (SEQ ID NOs: 16, 20, and 25) (Molhoek 2011). In another embodiment, methylene bridges, amide (peptide) bonds, or cysteine residues (disulfide bond) can be used to cyclize or attach two or more peptides together. This can be beneficial to constrain peptides into more stable conformations (Clark 2005). This also includes peptides or proteins with improved target specificity or binding, such as the optimal arrangement of amino acid residues in order to enhance molecular interactions between the ligand and receptor. In another embodiment, basic residues (Lys, Arg, or His) have been arranged such that interactions between the receptor and the ligand will be optimal. Also disclosed are proteins and peptides with improved (reduced) systemic toxicity. Cysteine residues often times dominate in peptides found to be toxic relative to other residues (Gupta 2013). In one such embodiment, the flanking cysteine residues of SEQ ID NO: 1 have been replaced with flanking leucine residues, and cyclization has been achieved by a methylene bridge between the flanking leucine residues.

Also disclosed are peptides and proteins that have amino acid sequence modifications or alterations resulting in better biopharmaceutical properties. The incorporation of acidic or basic side chains, for example, could improve the aqueous or non-aqueous solubility of peptides and proteins with enhanced formulations or pharmacokinetic properties (Rand 2012). In one embodiment, substitution of a residue with a low distribution coefficient (log D), such as aspartic acid, could be replaced with a residue with a greater log D value, such as leucine (SEQ ID NO: 31).

Also disclosed are peptides and proteins with improved cellular permeability. The addition of polyarginine sequences to peptides or proteins can greatly enable cellular uptake and permeability (Fuchs 2007), and the replacement of non-basic residues with arginine residues is also included. In one such embodiment, four of the nine existing residues contained in SEQ ID NO:1 have been replaced with arginine residues, enabling enhanced permeability while retaining efficacy (SEQ ID NO: 32).

Also disclosed are chimeric proteins containing a disclosed peptide fused to a heterologous protein. In one embodiment, the heterologous protein can have a therapeutic activity such as cytokine activity, cytotoxic activity or proapoptotic activity. In a further embodiment, the heterologous protein can be an antibody or antigen-binding fragment thereof. In other embodiments, the chimeric protein includes a peptide containing the amino acid sequence SEQ ID NOs: 2-34, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

I. Bifunctional Compounds

Also disclosed are bifunctional peptides which contain a homing peptide fused to a second peptide having a separate function. Such bifunctional peptides have at least two functions conferred by different portions of the full-length molecule and can, for example, display anti-angiogenic activity or pro-apoptotic activity in addition to selective homing activity.

If desired, an isolated peptide, or a homing molecule as discussed further elsewhere herein, can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be affected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl)benzoic acid (Mamb). Cyclization additionally can be affected, for example, through the formation of an lysinonorleucine bond between lysine (Lys) and leucine (Leu) residues or a dityrosine bond between two tyrosine (Tyr) residues. The skilled person understands that these and other bonds can be included in a cyclic peptide.

J. Combinatorial Techniques

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NOs: 2-33 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, CAR, are also disclosed. Thus, the products produced using the combinatorial or screening approaches that involve the disclosed compositions, such as, SEQ ID NOs: 2-33, are also considered herein disclosed.

K. Diseases

The disclosed compounds containing the CAR pharmacophore can be useful for the treatment and/or diagnosis of diseases such as: pulmonary diseases, pulmonary hypertension, interstitial lung disease, acute lung injury, acute respiratory distress syndrome, asthma, sepsis, septic shock, infection, sarcoidosis of the lung, pulmonary manifestations of connective tissue diseases, including systemic lupus erythematosus, rheumatoid arthritis, scleroderma, and polymyositis, dennatomyositis, bronchiectasis, asbestosis, berylliosis, silicosis, Histiocytosis X, pneumonia, pneumonitis, smoker's lung, bronchiolitis obliterans, pulmonary fibrosis, other fibrotic diseases such as myocardial infarction, endomyocardial fibrosis, mediastinal fibrosis, myelofibrosis, retroperitoneal fibrosis, progressive massive fibrosis, pneumoconiosis, nephrogenic systemic fibrosis, scar formation, keloid, arthrofibrosis, adhesive capsulitis, radiation fibrosis, fibrocystic breast condition, liver cirrhosis, hepatitis, liver fibrosis, nonalcoholic fatty liver disease, acute liver failure, nonalcoholic steatohepatitis, sarcoidosis of the lymph nodes, or other organs; inflammatory bowel disease, Crohn's disease, cachexia, chronic kidney disease, acute kidney injury, acute renal failure, polycystic kidney disease, ulcerative colitis, primary biliary cirrhosis, pancreatitis, interstitial cystitis, chronic obstructive pulmonary disease, atherosclerosis, ischemic heart disease, vasculitis, neoplastic/metastatic/oncological diseases (including cancer), pneumoconiosis, autoimmune diseases, angiogenic diseases, wound healing, infections, trauma injuries and systemic connective tissue diseases including systemic lupus erythematosus, rheumatoid arthritis scleroderma, polymyositis, dermatomyositis, cystic fibrosis, erectile dysfunction, α1-antitrypsin deficiency, diabetes, diseases characterized by high heparanase levels, neuroinflammatory conditions, stroke, CNS degenerative diseases, such as Alzheimer's Disease, Parkinson's disease (PD), Huntington's disease, amyotrophic lateral sclerosis, multiple sclerosis, traumatic brain injury, hypoxia, aging brain, wet macular degeneration, neovascular age-related macular degeneration, diabetic retinopathy, glioblastoma, senescence-related diseases and as a gene therapy adjuvant.

EXAMPLES

The following examples are meant to provide those of ordinary skill in the art with a disclosure and description of how some of the compounds, compositions, and/or methods claimed herein are made and evaluated. These examples are meant to be illustrative of broader approaches that could be used and are not intended to limit the disclosure in any way.

Example 1. Identification of the Cyclic CAR Pharmacophore

In an attempt to identify the cyclic CAR pharmacophore, cell binding and internalization assays for CAR peptide (SEQ ID NO: 1) and seven closely related peptides (SEQ ID NOs: 2-8) were performed.

1A. Confocal Microscopy.

Eight CAR variants (SEQ ID NOs: 1-8) with permutations on either the lysine or arginine residues were synthesized (FIG. 1). The peptides were labeled by attaching a fluorescamine (FAM) group to the molecule.

A cell binding and internalization assay was used as an initial test to compare the variants to the original CAR peptide. Cell binding/internalization by the CAR peptide variants was studied by confocal microscopy using Chinese Hamster Ovary (CHO-K) cells, which have been previously used to study CAR binding.

FAM-conjugated peptides as indicated were incubated at 5 µM concentration with CHO-K cells for 2 hours. The cells were washed, fixed, stained with the nuclear stain DAPI. The CHO cell binding and internalization results (FIG. 2) suggested that changing the first arginine into a lysine residue improves binding to the CHO cells, and that the peptide should have at least one arginine.

1B. Fluorescence-Activated Cell Sorting (FACS).

Eight CAR variants (SEQ ID NOs: 1-8) with permutations on either the lysine or arginine residues were synthesized (FIG. 1). The peptides were labeled by attaching a fluorescamine (FAM) group to the molecule.

To determine cell internalization of SEQ ID NOs: 1-8, fluorescence-activated cell sorting (FACS) was used. Human lung fibroblasts (CCL-210) were selected due to the fact that they appeared to be an even better target for CAR than the CHO cells. Unlike the confocal microscopy experiment (Example 1A), FACS analyses focuses entirely on peptide internalization, not peptide binding.

The cells were incubated with 5 µM peptides in serum-free DMEM at 37° C. for 24 hrs. After incubation, cells were washed 3-4 times with ice-cold buffer containing 100 µg/ml of heparin to remove any non-internalized peptide. The cells were detached using trypsin-EDTA, and the cell suspension was stained with 7AAD dye to ascertain cell viability. The cells were then immediately analyzed using FACS to determine the level of peptide internalization.

Figure 3:
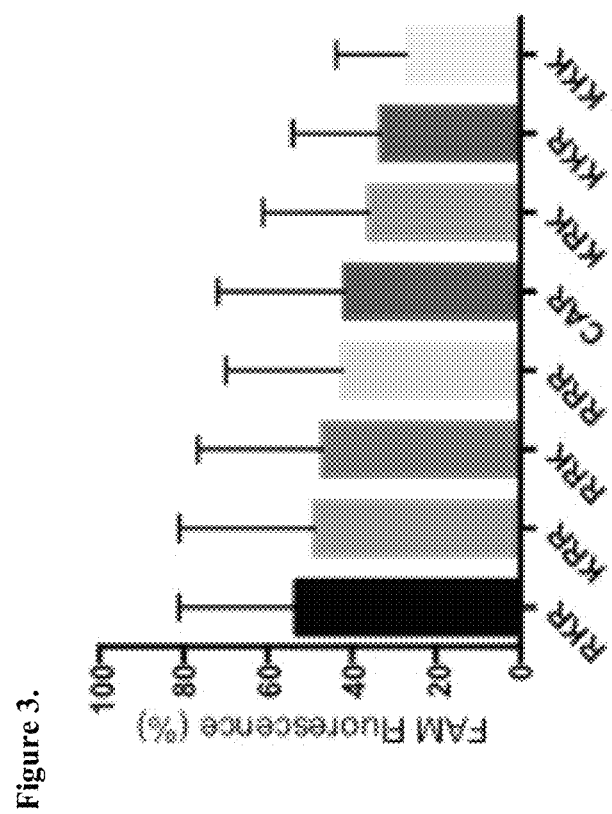
FIG. 3. CAR variant uptake into human lung fibroblasts (CCL-210). The cells were incubated with 5 µM peptides in serum-free DMEM at 37° C. for 24 hrs. After incubation, cells were washed 3-4 times with ice-cold buffer containing 100 µg/ml of heparin to remove any non-internalized peptide. The cells were detached using trypsin-EDTA, and the cell suspension was stained with 7AAD dye to ascertain cell viability. The cells were then immediately analyzed using FACS to determine the level of peptide internalization.
Figure 10:
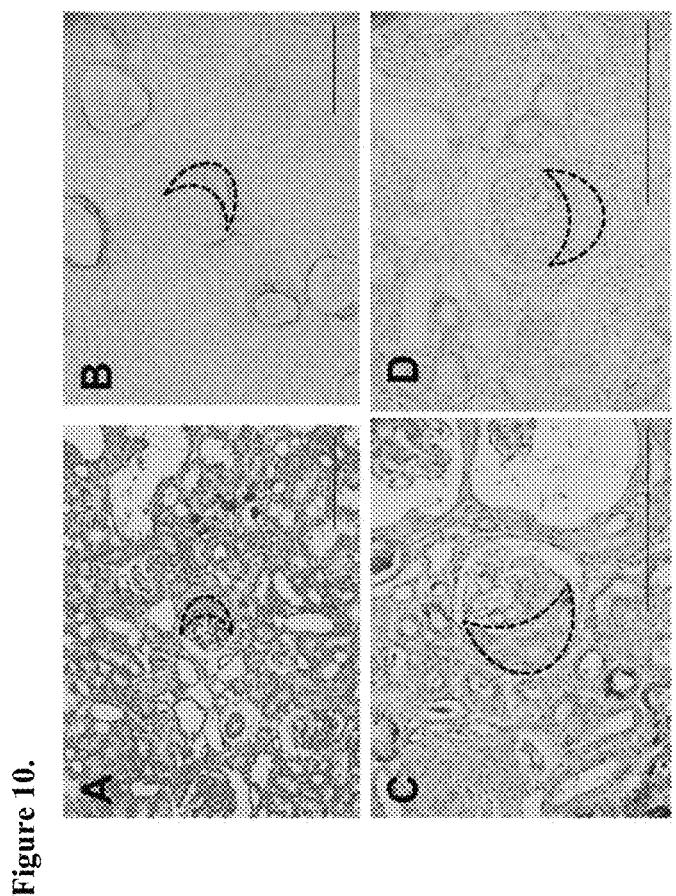

The FACS results identified variation in the peptide internalization profiles of SEQ ID NO: 1-8 based on the amino acid substitution present in each sequence (FIG. 3). Variation occurred in the intensity of peptide binding as well as in the localization of peptide binding. Interestingly, CAR pharmacophore peptide variants with conserved amino acid substitutions displayed differential binding and internalization characteristics between the CHO cells and human lung fibroblasts (as shown in FIGS. 2 and 3 respectively) indicating that conservative amino acid substitutions to the original CAR peptide produce unexpected differences in binding and internalization. These results unexpectedly teach away from the disclosure of Ruoslahti in U.S. Pat. No. 8,188,220 in which conservative amino acid substitutions were indicated to have little to no effect on peptide internalization.

The FACS results (Example 1B) differed from the confocal analyses (Example 1A) in that the two-arginine, one-lysine peptides were the most effective ones (FIG. 2). However, the background in this assay was high and the differences less than 50% and not statistically significant. The greater requirement for arginine residues than in the confocal study (Example 1A) may be related to the fact that we measured only internalization, not binding and internalization, in the FACS experiments (Example 1B). Multiple arginine residues are well known to promote internalization into cells.

1C. Computational Modeling Studies to Identify the Cyclic CAR Pharmacophore.

The experimental studies from Examples 1A and 1B revealed that SEQ ID NOs: 2-8 display similar biological activity to SEQ ID NO: 1. Based on the similarity of the structures of SEQ ID NOs: 2-8 to SEQ ID NO: 1, some initial clues to the essential features (pharmacophore) of SEQ ID NO: 1 that confer biological activity were obtained.

While there are differences in binding and internalization between the CAR variants, all of the variants were bound and internalized and the differences between variants were not statistically significant. Therefore, all eight variants possess similar biological activity to the original CAR sequence. Next, the essential features of the CAR pharmacophore were determined through in silico modeling.

All 8 of the CAR analogues (SEQ ID NOs: 1-8) were generated in silico using PyMOL Molecular Graphics System, Version 1.2r2 (PyMOL 2014). The various features of the created variants, such as steric properties, molecular weights, hydrogen bond donors and acceptors, accessible solvent surface area, sequence relationships, peptide backbone structure, and amino acid side chain location in space were all studied. Electronic similarities between SEQ ID NOs: 1-8 were studied using Adaptive Poisson-Boltzmann Solver (APBS) Version 1.2.1 (Baker 2001), a program that calculates the macromolecular electrostatics of molecules. The results of the calculation are rendered as an electrostatic potential molecular surface, and were useful for noting the similarities in the electrostatic charge distribution of all eight variants.

A variety of renderings were displayed in order to compare the various molecular features of SEQ ID NOs: 1-8. Of particular importance was the superimposition of SEQ ID NOs: 1-8, which demonstrated both trivial and subtle similarities between CAR peptide (SEQ ID NO: 1) and the CAR peptide analogues (SEQ ID NO: 2-8).

In analysis of the superimposed CAR analogues (FIG. 4), a conserved cyclic CAR structural pattern was seen that was identified as the cyclic CAR pharmacophore. This is due to the striking structural, electronic, steric, and sequential similarities of SEQ ID NOs: 1-8. These results confirm the data generated in Example 1, where SEQ ID NOs: 2-8 display similar biological activity to SEQ ID NO: 1, the original CAR sequence (SEQ ID NO: 1), and all sequences fit within the CAR pharmacophore.

Example 2. Creation of Novel Non-Peptide Compounds that Possess the Cyclic or Linear CAR Pharmacophore Using Peptidomimetics 2A. In Silico Generation and Virtual Rendering of SEQ ID NOs: 9-11 and 13-15.

In an effort to illustrate a peptidomimetic approach that could be taken to create a novel compound that possesses the CAR pharmacophore, a small compound library in silico was generated using PyMOL Molecular Graphics System, Version 1.2r2 (PyMOL 2014). Six structures have been designed to contain the CAR pharmacophore required for disease homing and selective internalization. Utilizing a rational approach to mimic CAR's molecular properties, all six of the analogues were produced from three existing, widely available therapeutics: voclosporin, rapamycin, and rifabutin. Three cyclic variants were produced containing the cyclic CAR pharmacophore (SEQ ID NOs: 9-11), and three linear variants were produced which contain the linear CAR pharmacophore (SEQ ID NOs: 13-15).

Although certain aspects of voclosporin, rapamycin, and rifabutin may differ from that of CAR (for example, rapamycin, and rifabutin are non-peptide compounds), these molecules can be a starting point for a peptidomimetic approach to producing CAR analogues. These compounds were chosen on the bases of their cyclic nature, molecular weight (approx. 1 kDa), and oral bioavailability, all of which are characteristics of CAR peptide as well.

The various features of SEQ ID NOs: 9-11 and SEQ ID NOs: 13-15 were studied, such as steric properties, molecular weights, hydrogen bond donors and acceptors, accessible solvent surface area, sequence relationships, cyclic ring backbone structure, and amino acid side chain/functional group location in space. The observed characteristics of SEQ ID NOs: 9-11 and 13-15 were compared to cyclic CAR and linear CAR respectively, in order to determine if these analogues would still possess the CAR pharmacophore and CAR peptide's disease homing and selective internalization properties. The modifications to the analogues would enable these compounds to possess similar binding, internalization, and disease selectivity as the CAR pharmacophore.

2B. Analysis of Results.

When comparing cyclic CAR (SEQ ID NO: 1) with cyclic CAR-Rapamycin (SEQ ID NO: 9), cyclic CAR-Rifabutin (SEQ ID NO: 10), and cyclic CAR-Voclosporin (SEQ ID NO: 11), it can be seen that both similarities and differences between all four compounds exist. Obviously, the non-peptide/small molecule nature of SEQ ID NOs: 9 and 10 account for most of the observable difference between them and SEQ ID NO: 1. However, upon closer inspection of SEQ ID NOs: 1 and 9-11, it can be seen that a conserved pattern of steric features exist. More specifically, it is apparent that three specific functional groups, all with a positively charged terminus, are present in each of the cyclic peptidomimetics. The functional groups of each analogue all protrude out from the core backbone structure (the cyclic ring) into space, in a similar manner as SEQ ID NO: 1. Electrostatic similarities between SEQ ID NOs: 1 and SEQ ID NOs: 9-11 also exist, with particular emphasis on the positively charged components of the extended functional groups. Other similarities between SEQ ID NOs: 1 and SEQ ID NOs: 9-11 also exist, including molecular weights and retained cyclic, ring-like structures comprising the core backbone structure.

Analysis of linear CAR (SEQ ID NO: 12) with linear CAR-Rapamycin (SEQ ID NO: 13), linear CAR-Rifabutin (SEQ ID NO: 14), and linear CAR-Voclosporin (SEQ ID NO: 15), showed that both similarities and differences exist between all four compounds. As with the cyclic structures previously observed (SEQ ID NOs: 9-11), it can be seen that a conserved pattern of steric features exist between linear CAR (SEQ ID NO: 12) and the linear analogues (SEQ ID NOs: 13-15). Three unique functional groups, all with a positively charged terminus, are present in each of the linear peptidomimetics. These functional groups of each analogue all protrude out from the linear backbone of the structure into space, in a similar manner as SEQ ID NO: 12. Electrostatic similarities between SEQ ID NOs: 12 and SEQ ID NOs: 13-15 can also be seen, with all four compounds possessing a positively charged region at the terminus of the extended three functional groups.

The results from both the linear and cyclic CAR peptidomimetics library serves as a non-limiting, illustrative approach that could be employed when utilizing peptidomimetics to generate compounds, including small molecules, that posses the CAR pharmacophore and disease homing and selective internalization properties of CAR peptide. The molecules may also possess their original therapeutic properties combined with the homing and disease selectivity properties of the CAR pharmacophore. In addition, Example 3 serves to further define the previously identified CAR pharmacophore, which is not only be defined in terms of precise sequences and residue patterns, but can also be defined in terms of more generalized structures that possess similar three-dimensional spatial, steric, and electronic patterns as linear, truncated, and cyclic CAR peptides.

Example 3. Creation of Novel Peptide
Substitutional Variants Containing the Cyclic,
Linear, and Truncated CAR Pharmacophore 3A. In Silico Generation and Virtual Rendering of SEQ ID NOs: 16-19, 20-23, and 25-28.

In an effort to illustrate a substitutional approach that could be taken to create novel peptides that possesses the CAR pharmacophore, a focused compound library in silico was generated using PyMOL Molecular Graphics System, Version 1.2r2 (PyMOL 2014). In this example, all cyclic, linear, and truncated analogues that were generated contain unnatural amino acid substitutions. The specific unnatural amino acid residues used, as well as their location within the CAR peptide sequence, were all deliberately chosen, in order to produce novel analogues that still retain the CAR pharmacophore. SEQ ID NOs: 16-19 were designed to fit the cyclic CAR pharmacophore, SEQ ID NOs: 20-23 were designed to fit the linear CAR pharmacophore, and SEQ ID NOs: 25-28 were designed the truncated CAR pharmacophore.

There were 12 substitutional variants generated in total: 4 cyclic, 4 linear, and 4 truncated. The types of substitutions that were performed are the same for the cyclic, linear, and truncated variants. More specifically, within each category (cyclic, linear, and truncated), one analogue was produced by altering the stereochemistry of the first Lys residue in the CAR amino acid sequence, resulting in a D-amino acid substitution at this position. Another analogue was produced for each category containing a D-allylglycine residue (a type of glycine derivative) in place of the normal Ala residue. Diamino acid substitution was also generated within each category, where the Arg residue of the CAR sequence was replaced with an Asn residue. Finally, substitutional variants were produced in which the Cys residue of the CAR sequence (which normally contains a charged or acetylated N-term) was substituted for a N-methylated Cys residue.

The molecular features of SEQ ID NOs: 16-19, 20-23, and 25-28 were studied, including steric properties, molecular weights, hydrogen bond donors and acceptors, accessible solvent surface areas, sequence relationships, backbone structure, and amino acid side chain/functional group location in space. Observed characteristics of SEQ ID NOs: 16-19, 20-23, and 25-28 were compared to their respective cyclic, linear, or truncated CAR counterparts in order to determine if the analogues would still possess the CAR pharmacophore and would thus possess CAR peptide's disease homing and selective internalization properties.

Several virtual renderings were created in order to convey the various molecular similarities of cyclic, linear, and truncated CAR peptides with their respective substitutional analogues.

3B. Analysis of Results.

The superimposition of cyclic CAR (SEQ ID NO: 1) with the cyclic substitutional analogues (SEQ ID NOs: 16-19) allows for the similarities of all five compounds to be seen (FIG. 7). The amino acid substitutions in SEQ ID NOs: 16-19 did not result in loss of cyclic ring structure or spatial placement of the positively charged basic residues. The fact that all three basic residues (Arg, Lys1, and Lys2) have nearly identical side chain spatial placements as SEQ ID NO: 1 demonstrates that SEQ ID NOs: 16-19 possess the cyclic CAR pharmacophore. Additionally, electrostatic similarities between SEQ ID NOs: 1 and SEQ ID NOs: 16-19 are seen, with particular emphasis on the positively charged components of the extended side chains. Other more trivial similarities between SEQ ID NOs: 1 and SEQ ID NOs: 16-19 also exist, including molecular weights and retained cyclic, ring-like structures comprising the core backbone structure.

When analyzing linear CAR (SEQ ID NO: 12) and the linear substitutional variants (SEQ ID NOs: 20-23), a great deal of similarities can be seen between all five compounds (FIG. 8). The amino acid substitutions in SEQ ID NOs: 20-23 did not result in loss of linear backbone structure, and the three-dimensional spatial placement of the positively charged basic residues (Arg, Lys1, and Lys2) are nearly identical to that of SEQ ID NO: 12. The electrostatic similarities between SEQ ID NOs: 12 and SEQ ID NOs: 20-23 are also apparent, including the positively charged components of the extended Arg and Lys side chains. The results of the analysis show that SEQ ID NOs: 20-23 possess the linear CAR pharmacophore.

The superimposition of truncated CAR (SEQ ID NO: 24) with the truncated substitutional analogues (SEQ ID NOs: 25-28) allows for the similarities of all five compounds to be seen (FIG. 9). As with the linear analogues produced, the residue substitutions in SEQ ID NOs: 25-28 did not result in loss of linear backbone structure, and the three-dimensional spatial placement of the positively charged basic residues (Arg, Lys1, and Lys2) are nearly identical to that of SEQ ID NO: 24. The electrostatic similarities between SEQ ID NOs: 24 and SEQ ID NOs: 25-28 can be seen, including the positively charged components of the extended Arg and Lys side chains. Given these essential similarities between SEQ ID NOs: 25-28 and SEQ ID NO: 24, it has been deduced that SEQ ID NOs: 25-28 possess the truncated CAR pharmacophore.

Example 4. Development of Conjugated Compounds which Possess the Cyclic and Truncated CAR Pharmacophore 4A. In Silico Generation and Virtual Rendering of Conjugated Compounds.

Two novel compounds containing the CAR pharmacophore were generated in silico using PyMOL Molecular Graphics System, Version 1.2r2 (PyMOL 2014). Compound 1 consists of the human serum albumin (HSA; SEQ ID NO: 29) protein which has been linked (conjugated) to truncated CAR peptide (tCAR; SEQ ID NO: 24). Compound 2 consists of the Fv fragment of the monoclonal anticancer antibody B1 (SEQ ID NO: 30, 35) which has been conjugated to cyclic CAR (SEQ ID NO: 1).

Compound 1 was produced by conjugating tCAR to the free sulfhydryl group at the Cys34 residue of human serum albumin (HSA; SEQ ID NO: 29) via a disulfide bond. This HSA-tCAR conjugate has previously been shown to prolong the half-life of tCAR (Dennis 2002), and is illustrative of a much broader approach that can be used to enhance the properties, such as half-life, of a CAR pharmacophore variant. Compound 2 was produced by covalently linking (via a peptide bond) cyclic CAR peptide to the Fv fragment of the monoclonal anticancer antibody B1 (SEQ ID NO: 30, 35). This antibody has an affinity for human carcinoma cells. The bifunctional compound would result in a drug conjugate with a high degree of specificity to human cancer cells, and is illustrative of a broader class of compounds containing the CAR pharmacophore that would possess both disease homing and therapeutic properties.

Example 5. Creation of Peptides with Optimized Properties that Contain the Cyclic CAR Pharmacophore 5A. In Silico Generation and Virtual Rendering of SEQ ID NOs: 31-33.

In an effort to illustrate a computer-aided optimization approach that could be taken to develop novel peptides that possesses the cyclic CAR pharmacophore, a compound library in silico was generated using PyMOL Molecular Graphics System, Version 1.2r2 (PyMOL 2014). In addition to possessing the CAR pharmacophore, all three analogues produced (SEQ ID NOs: 31-33) contain one or more chemical modifications that would result in the creation of a structure with improved or enhanced properties. The structures produced may possess more than one improved feature resulting from a single type of sequential modification. In the process of producing SEQ ID NOs: 31-33, techniques previously disclosed were often employed, including substitutional modifications.

SEQ ID NO: 31 was produced by substituting the flanking C-terminus and N-terminus Cys residues of SEQ ID NO: 1 with Leu residues to produce the amino acid sequence: LARSKNKDL. In this case, cyclization has been achieved via a methylene bridge joining the two flanking Leu residues, opposed to the normal disulfide linkage of SEQ ID NO: 1. Like the disulfide bond in SEQ ID NO: 1, the modification serves to constrain the peptide into a more stable conformation. However, unlike the disulfide bond in SEQ ID NO: 1, the two Leu residues could potentially reduce any systemic toxicity associated with SEQ ID NO: 1, due to the fact that Leu residues, generally speaking, have a lower level of systemic toxicity that Cys residues (Gupta 2013).

SEQ ID NO: 32 was generated by rearranging and replacing the original amino acid sequence of SEQ ID NO: 1 to produce the sequence: CAKSRNHDC. More specifically, the Arg1 of SEQ ID NO: 1 has been replaced with a Lys residue; the Lys1 of SEQ ID NO: 1 has been replaced with an Arg residue; and the Lys2 of SEQ ID NO:1 has been replaced with a His residue. Given the unconfirmed nature of CAR peptide's receptor and mechanism of internalization, this rearrangement/replacement could produce an optimal arrangement of amino acid residues which will enhance the molecular interactions between the ligand and receptor. This ultimately could result in improved target specificity, binding, or internalization of this compound containing the cyclic CAR pharmacophore.

SEQ ID NO: 33 was produced by substituting the negatively charged Asp residue of SEQ ID NO: 1 with the hydrophobic Leu residue, yielding the amino acid sequence: CARSKNKLC. Substitution of a residue with a low distribution coefficient (log D), such as aspartic acid, with a residue with a greater log D value, such as leucine, would improve the non-aqueous solubility of the peptide, and could potentially result in production of an analogue capable of enhanced formulations or improved pharmacokinetic properties (Rand 2012).

5B. Analysis of Results.

The superimposition of cyclic CAR (SEQ ID NO: 1) with the optimized peptide analogues (SEQ ID NOs: 31-33) allows for the visualization of the similarities between all five compounds (not shown). The amino acid substitutions in SEQ ID NOs: 31-33 did not result in loss of cyclic ring structure or spatial placement of the positively charged basic residues. The fact that all three basic residues (Arg, Lys1, and Lys2) have nearly identical side chain spatial placements as SEQ ID NO: 1 demonstrates that SEQ ID NOs: 31-33 possess the cyclic CAR pharmacophore Additionally, electrostatic similarities between SEQ ID NOs: 1 and SEQ ID NOs: 31-33 are seen, with particular emphasis on the positively charged components of the extended side chains. Other more trivial similarities between SEQ ID NOs: 1 and SEQ ID NOs: 31-33 also exist, including molecular weights and retained cyclic, ring-like structures comprising the core backbone structure.

Example 6: Potential CAR Variant Development

CAR contains 3 basic residues in a Basic-X-Basic-X-Basic-X configuration. This motif is similar to heparin binding motifs in a number of proteins. Given the requirement for heparan sulfate binding for CAR (Jarvinen and Ruoslahti, 2008), permutations were made in order to preserve a basic amino acid (either arginine or lysine) in the original positions. The rest of the positions were varied randomly. Mutation analysis in phage was performed because it is the most facile way of performing such an analysis. The phage clones were tested for binding to CHO cells (Jarvinen and Ruoslahti, 2010), and when active, for in vivo homing. In parallel, truncated CAR sequences were also examined. Prior experiments found that a linear peptide truncated at the C-terminus to CARSKNK (from CARSKNKDC) is highly active in cell binding and tissue homing. In contrast, truncating the N-terminus reduced the activity. These results define the pharmacophore as XXBXBXB, where B is a basic amino acid. The X residues was randomly mutated and phage was tested in order to arrive at the shortest and/or most active peptides.

The results showed that in the motif CxRxRxR, "R" can be K or R, namely residues with positively side groups. Cell binding and cell homing was not improved where "R" was D, E, H, T, S, N, I, V, G, Q, L, and P. For "X" it was more difficult to interpret which residues result in improved cell binding and cell homing. Results indicated that "X" cannot be P. Frequently electrostatic differences, and not actual bonding distances, led to a negative conclusion for "X" being K, H, R, D, E, C, F, W or Y. Finally, results showed that "X" can be T, S, N, Q, A, I, L or V, namely residues with polar, uncharged side groups as well as residues with hydrophobic side groups.

Example 7: CAR Pharmacophore Targeting of Chronic Kidney Disease

A rat model of crescentic glomerular nephritis (anti-glomerular basement membrane antibody induced glomerular injury) was used to observe the utility of CAR pharmacophore targeting in chronic kidney disease. Glomerulonephritis was induced in rat kidneys by i.v. injection of anti-glomerular basement membrane antibodies. 14 days after induction, CAR pharmacophore peptide or control (CGGGGGGGC SEQ ID NO: 34) peptide was i.v. injected at 3.3 mg/kg B.W. Kidneys were harvested three hours after CAR pharmacophore or control injection and Masson's trichrome (collagen) staining and fibronectin immunostaining were used to determine development of kidney disease and fibrosis formation.

The results shown in FIG. 10 suggest a utility for CAR pharmacophore in targeting chronic kidney disease. CAR pharmacophore accumulated extensively (purple) in glomerular capillaries, crescents in Bowman's space, tubular epithelium, and interstitium (C) in the diseased kidney. CAR pharmacophore accumulated in crescent as well as renal tubes. Renal tube accumulation may be related to reabsorption. In comparison, the control peptide was largely cleared from the kidney at 3 hours administration (D).

Example 8

CAR pharmacophore co-administration with imatinib in a rat model of monocrotaline-induced (MCT) PAH was used to observe the therapeutic utility of CAR for targeting PAH. CAR pharmacophore peptide was intravenously co-administered with 10 mg/kg or 50 mg/kg imatinib for 14 days starting 4 weeks post MCT induction.

The results suggest that the severity of MCT-induced PAH was not as great as in previously reported studies at 4 weeks post induction following the co-administration of CAR pharmacophore and imatinib (data not shown). The co-administration of CAR pharmacophore enhanced the effects of imatinib to reduce right-hear hypertrophy.

Similarly, when the degree of pulmonary artery muscularization was measured in this experiment, the co-administration of CAR pharmacophore enhanced the effects of imatinib (data not shown).

A surprising result was the discovery of CAR pharmacophore's beneficial effect on body weight. The reduction in right-heart hypertrophy and pulmonary artery muscularization coincided with improved bodyweight recovery of the hypertensive rats. Cachexia, or wasting syndrome, is the loss of weight, muscle atrophy, fatigue, weakness, and loss of appetite in an individual not actively trying to lose weight. Cachexia is seen in n patients with cancer, AIDS, chronic obstructive lung disease, multiple sclerosis, congestive heart failure, tuberculosis, familial amyloid polyneuropathy, mercury poisoning (acrodynia) and hormonal deficiency. The discovery of CAR pharmacophore's beneficial effect on body weight provides initial evidence of CAR pharmacophore's ability to ameliorate weight loss induced by MCT injection and possibly even cachexia in general.

Figure 11:
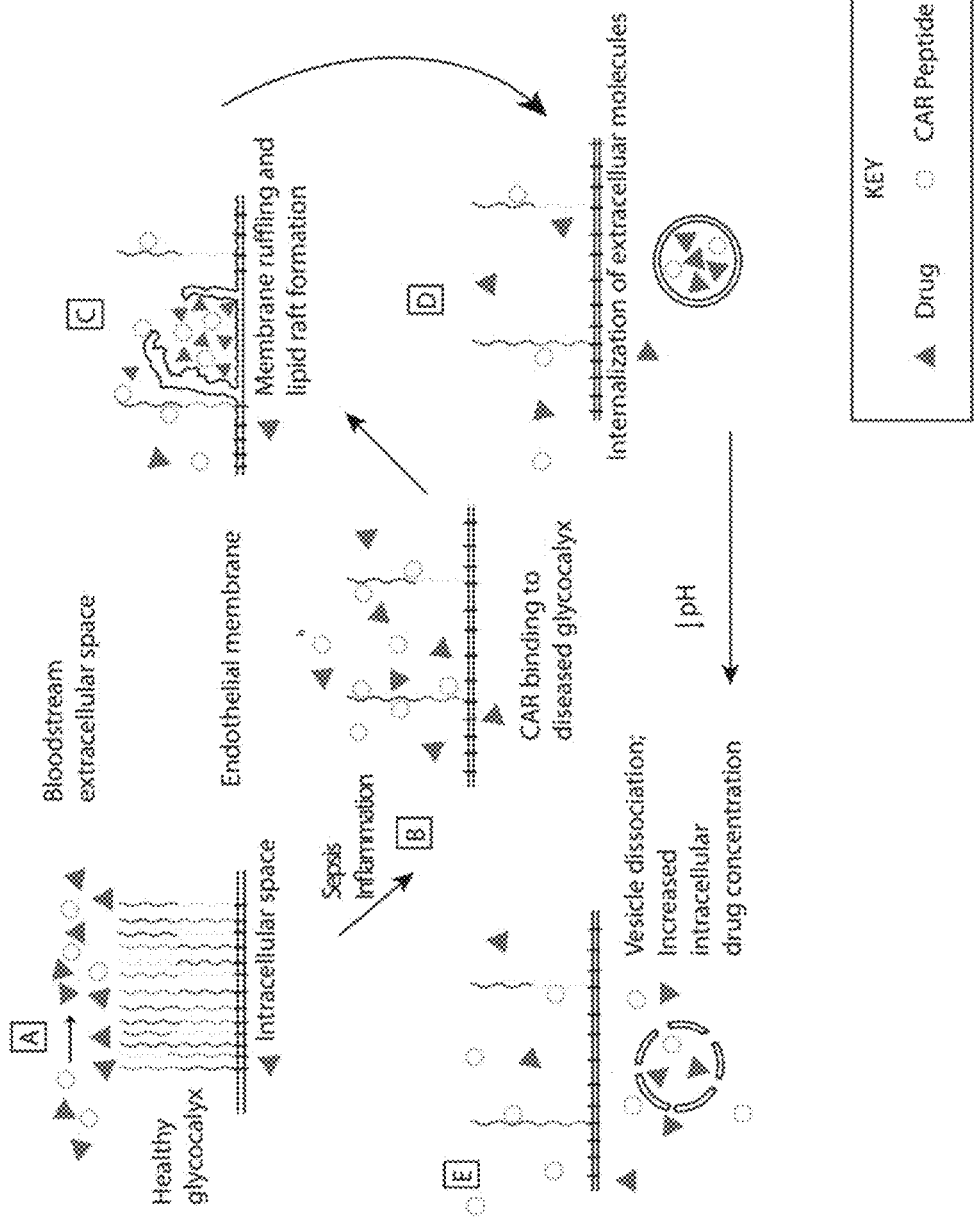

Example 9: CAR Pharmacophore Ability to Improve Sepsis Survival in a Lipopolysaccharide Endotoxin (LPS) Mouse Model of Sepsis Hypothesized Mechanism of CAR Action in sepsis (FIG. 11). (A) Healthy glycocalyx of endothelial membranes does not bind CAR peptide. Some drug molecules passively diffuse through the plasma membrane but majority of drug remains in bloodstream. (B) After sepsis, heparanase expression causes selective enzymatic cleavage of heparan sulfate (HS) chains and modification of the glycocalyx. HS variants resistant to cleavage remain intact, allowing CAR to bind to its HS receptors. (C) Binding of CAR triggers membrane ruffling and lipid raft formation, causing inward folding of the plasma membrane and engulfing of extracellular components including CAR and drug molecules. (D) Macropinocytic vesicles containing CAR and drug molecules are internalized into the cell. (E) Reduced intracellular pH causes the macropinosome to dissociate, releasing CAR and drug into the cell. While this is still just a hypothesis, it could explain how CAR selectively enhances the localized activity of drugs in septic tissues without increasing vascular permeability.

Fifty-percent of all mice with LPS-induced sepsis that are left untreated are dead within 48 hours. When these LPS mice are treated with clinically relevant doses of the common and experimental sepsis drugs hydrocortisone, antithrombin III or sivelestat, survival ranged from 40-56%, similar to current clinical outcomes. In contrast, when LPS mice were co-administered CAR at the same time as hydrocortisone, antithrombin III or sivelestat, experimental sepsis survival improved to 83-89%.

Figure 12:
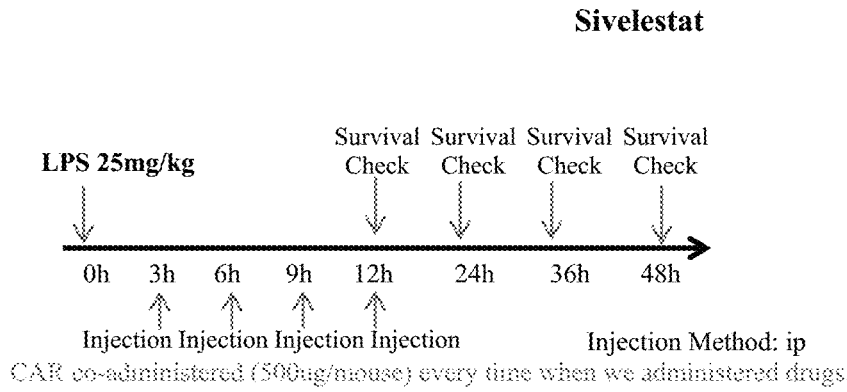

CAR pharmacophore dramatically improved survival in septic mice treated with sivelestat. Injection of the bacterial protein, lipopolysaccharide (LPS), was used to induce sepsis in mice. Doses were given at 3, 6, 9, and 12 hours to match the clinical use of sivelestat. Survival was measured up to 48 hours after LPS injection. At 48 hours, the survival rate of CAR pharmacophore+sivelestat treated animals was 89% compared to 50% in both control and sivelestat only groups, representing a 78% increase in survival of animals treated with CAR pharmacophore (FIG. 12).

Figure 13:
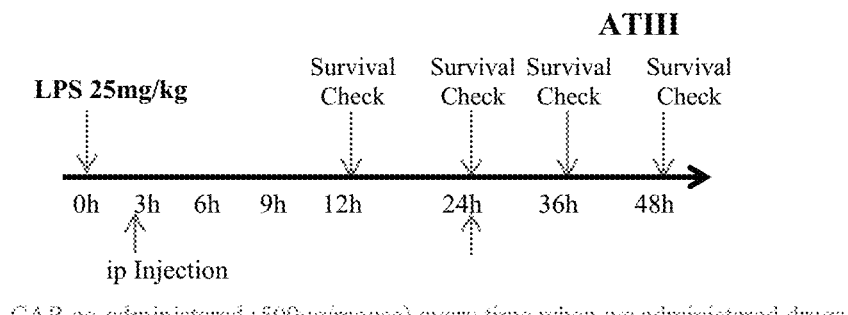

CAR pharmacophore dramatically improved survival in septic mice treated with antithrombin III (ATIII). Sepsis was initiated and survival measured with doses given at 3 and 24 hours to match the clinical use of ATIII. At 48 hours, the survival rate of CAR pharmacophore+ATIII treated animals was 83% compared to 50% in control and 40% in ATIII only groups, representing a 66% increase in survival of CAR pharmacophore treated animals over the ATIII only group (FIG. 13). The decreased survival of ATIII only animals could be due to hemorrhage caused by ATIII's anti-coagulant activity. CAR pharmacophore appeared to completely reverse this effect.

Figure 14:
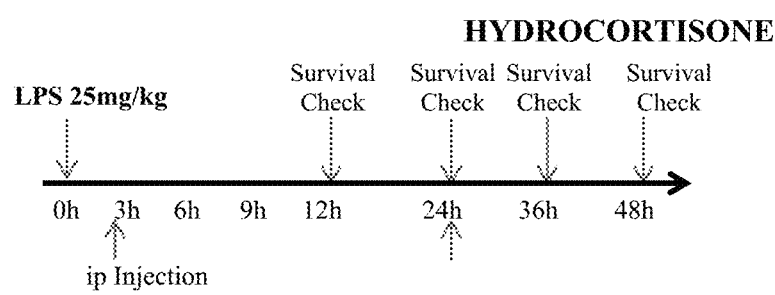

CAR pharmacophore dramatically improves survival in septic mice treated with hydrocortisone steroid. Sepsis was initiated and survival measured with doses given at 3 and 24 hours to match the clinical use of hydrocortisone. At 48 hours, the survival rate of CAR pharmacophore treated animals was 83% compared to 50% in control and 56% in hydrocortisone only groups, representing a 57% increase in survival of CAR pharmacophore treated animals over the hydrocortisone only group (FIG. 14).

Encouraged by this result we then tested CAR pharmacophore by itself in LPS sepsis mice and survival improved to 80%. CAR pharmacophore as a stand-alone therapeutic in sepsis found that CAR pharmacophore, administered alone via intraperitoneal injection at 20 mg/kg (or 500 ug/mouse) to LPS-mice improved survival rates from 50% (no treatment) to 80% with CAR pharmacophore at 48 hours. This demonstrates CAR pharmacophore's utility to enhance existing sepsis therapies as well as its potential as a stand-alone agent to improve sepsis survival. The CAR pharmacophore dose administered, i.e. 500 ug/20-25 g mouse, is equivalent to 20-25 mg/kg of CAR pharmacophore by body weight, supporting the potential of CAR pharmacophore by itself acting as a powerful anti-inflammatory agent that induced localized micropinocytosis in inflamed tissues characterized by an altered glycocalyx resulting in the inflamed tissue being able to uptake extracellular molecules at a rate more similar to normal tissue thereby allowing the tissue to heal from inflammation.

Figure 16:
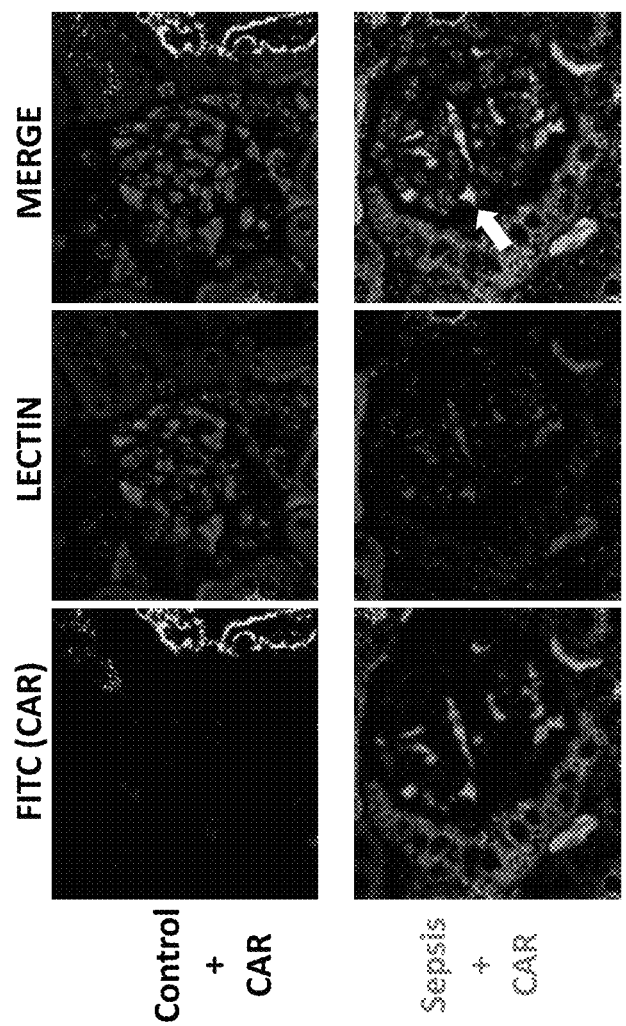

Example 10: CAR Pharmacophore Targeting in Sepsis and Restoration of Damaged Lung, Liver and Kidney Endothelium LPS injection was used to induce sepsis in 10 week old male C57BL6 rats (20 mg/kg, ip). Animal survival was assessed 48 h after injection: PBS 100% (n=10), LPS 21.4% (n=28), p<0.05 (FIG. 15A). In order to confirm whether CAR pharmacophore homes to endothelial cells, animals were treated with fluorescent CAR pharmacophore-FAM (8 mg/kg ip) 12 hours after receiving either PBS or LPS. Animals were sacrificed one hour later and the lung, liver, and kidney tissues were processed for histology. CARpositive staining was observed exclusively in pulmonary vessels and Glisson's sheath in the liver of septic animals (FIG. 15B, arrows). In the kidney, higher levels of CAR pharmacophore was concentrated in the glomeruli of septic animals (arrows). As shown in FIG. 16, CAR pharmacophore co-localizes with the endothelial specific marker lectin in the kidney. In septic animals, CAR pharmacophore homes to damaged endothelial cells and co-localizes with lectin (arrow).

Figure 17:
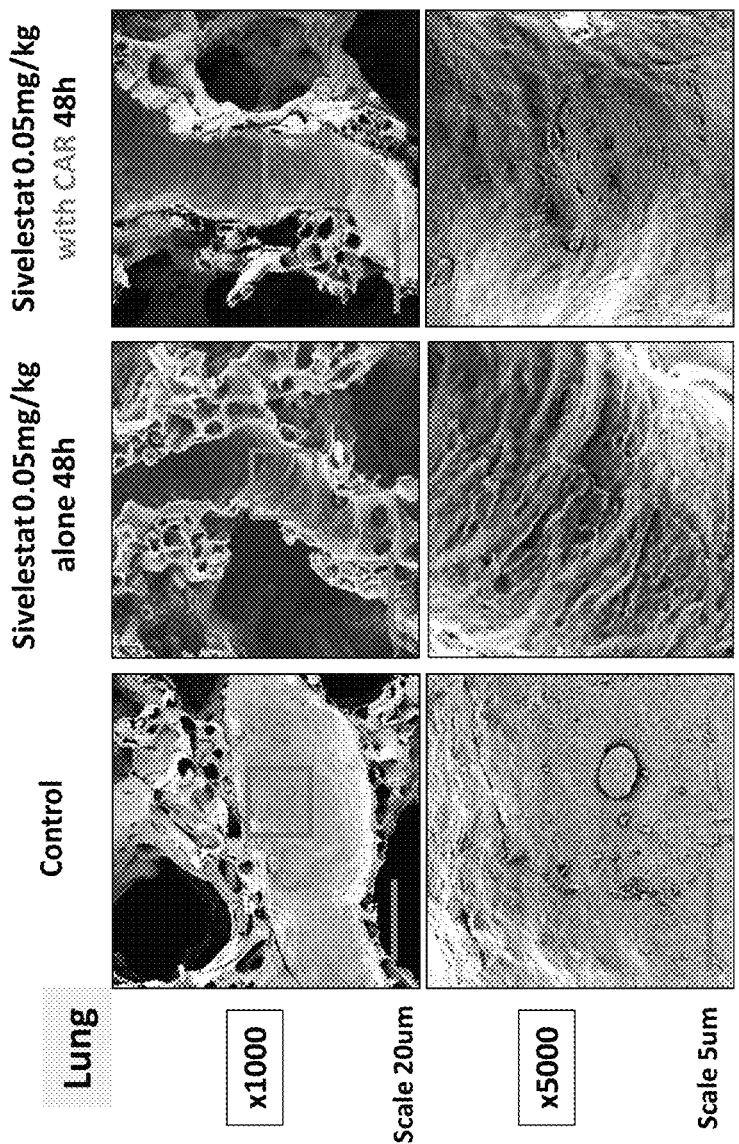

Scanning electron micrograph of lung tissue from control, sivelestat and CAR pharmacophore+sivelestat treated mice indicated that sivelestat alone did not prevent degradation of the continuous pulmonary arteriole endothelium (FIG. 17). When CAR pharmacophore was co-administered with sivelestat, degradation of the endothelium was prevented and its continuous appearance was similar to control.

Figure 18:
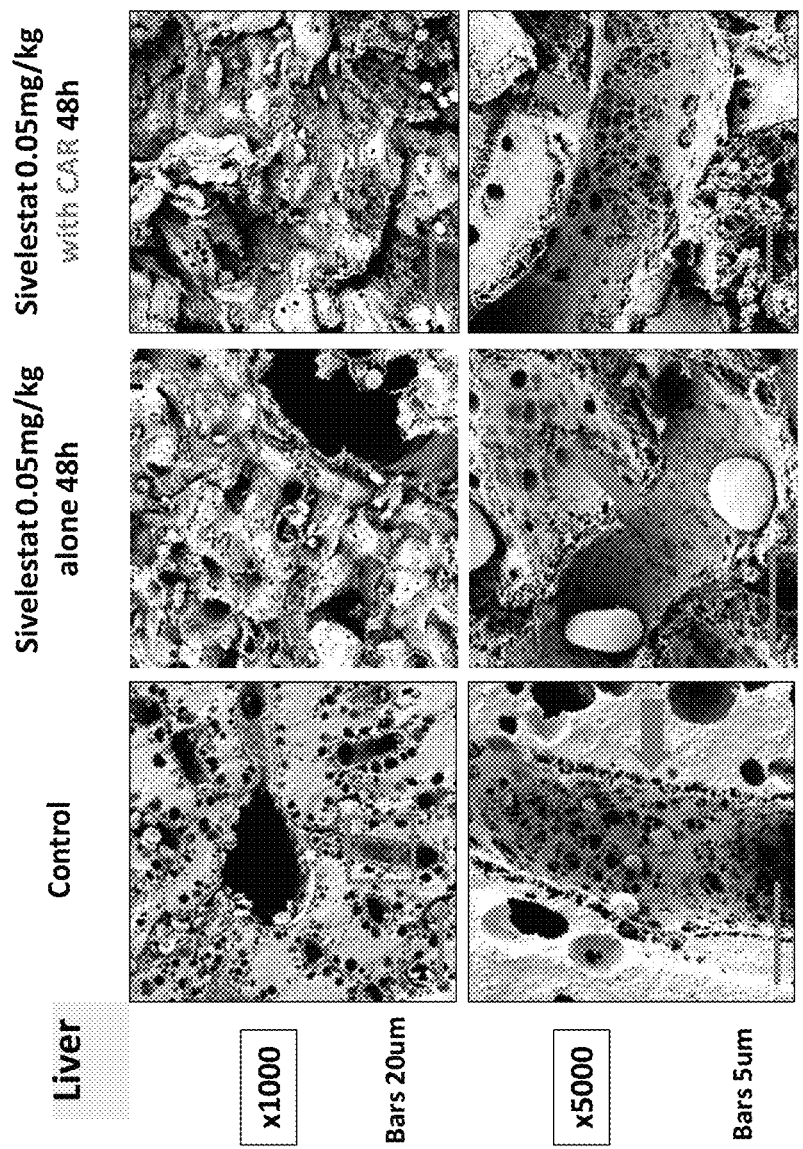

Scanning electron micrograph of liver tissue from control, sivelestat and CAR pharmacophore+sivelestat treated mice indicated that sivelestat alone was not able to prevent defenestration of sieve plates in septic animals as shown in the control (FIG. 18). When CAR pharmacophore was co-administered with sivelestat to septic animals, the size and number of sieve plate clusters is restored to almost control levels.

Figure 19:
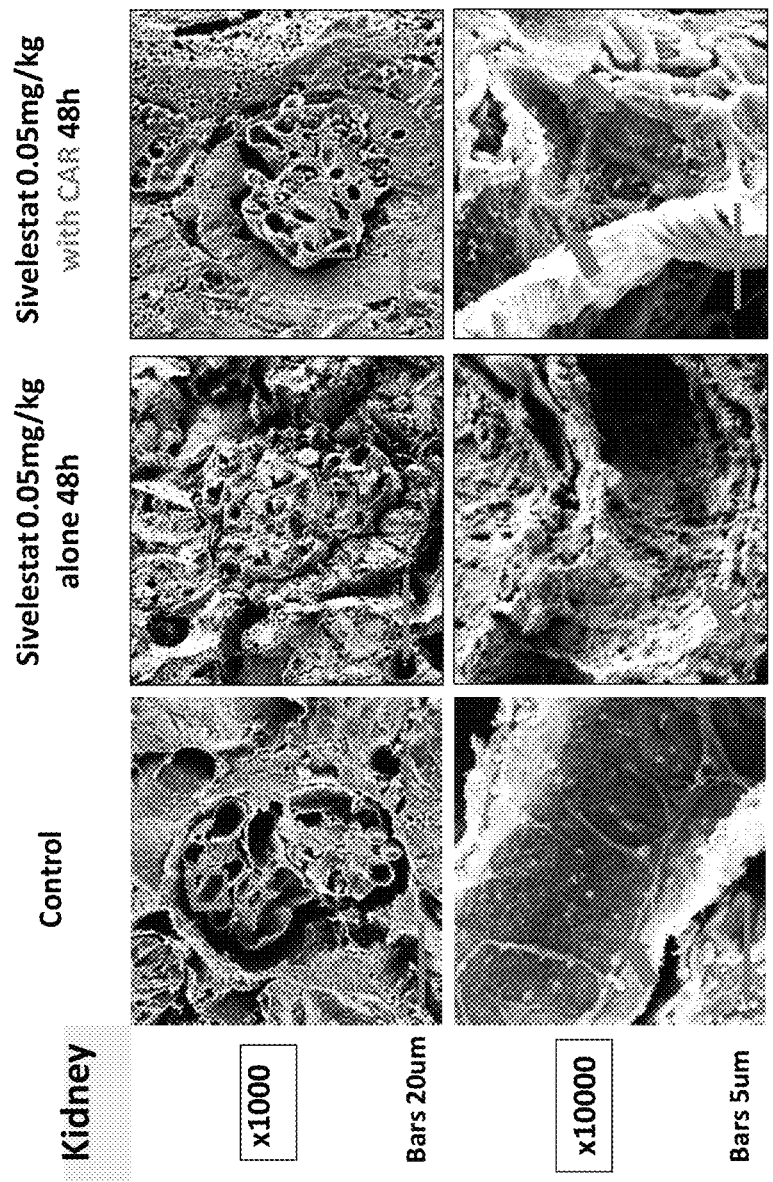

Scanning electron micrograph of kidney tissue from control, sivelestat and CAR pharmacophore+sivelestat treated mice indicated that sivelestat alone did not prevent gross tissue damage (arrow) as shown in the control (FIG. 19) presumably due to activation of neutrophil elastase which leads to proteolytic degradation of critical extracellular matrix proteins. When CAR pharmacophore was co-administered with sivelestat, sivelestat's anti-elastase appears to be efficiently boosted by CAR pharmacophore's selective homing to the injured endothelial glycocalyx in the kidney.

Figure 20:
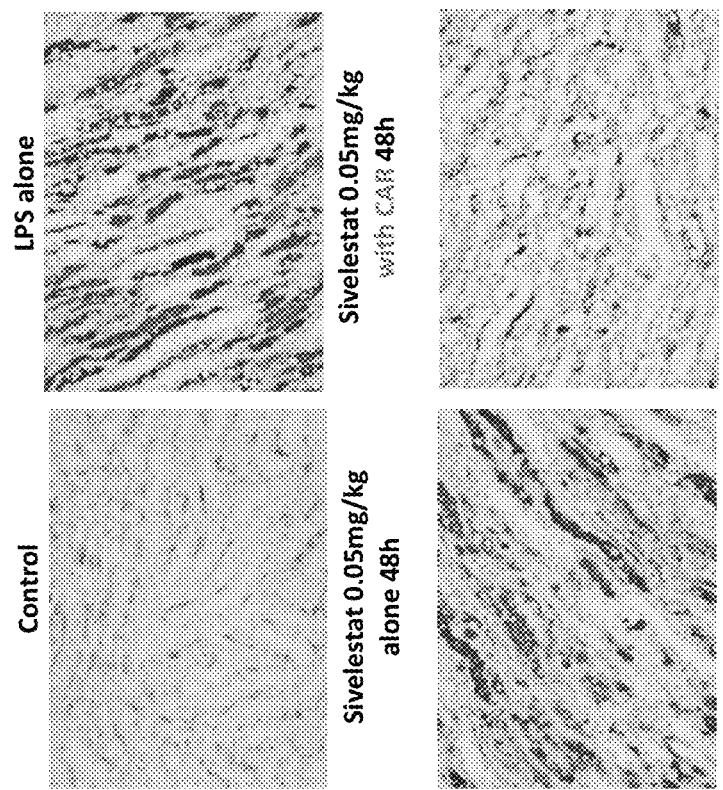

Acute Kidney Injury Marker (KIM-1) expression decreased in the CAR pharmacophore treated animals (FIG. 20). Histological staining for KIM-1 which is upregulated in the proximal tubule upon kidney injury is markedly reduced in CAR pharmacophore treated animals.

Example 11: Effect of CAR Pharmacophore in Triple Negative Breast Cancer Model

In female athymic nude mice (CRL: NU(NCr)—Foxn1nu, 11 weeks old, Charles River), triple negative breast cancer tumors were initiated via subcutaneous injection of 5×106 MDA-MB-231 cells into the right flank. Tumor growth was monitored until the average tumor size approached 100-150 mm3. Twenty one days after tumor implantation (Day 1 of study, weight range 20.6 to 27.3 grams), animals were sorted into three groups (n=3) receiving either a combination of paclitaxel and CAR pharmacophore (3 mg/kg each), paclitaxel (3 mg/kg), or saline vehicle. Animals were dosed intravenously every other day for a total of 15 doses. Tumor volume was measured using calipers twice per week and animals weighed daily on days 1-5 and then on a twice weekly schedule.

Figure 21:
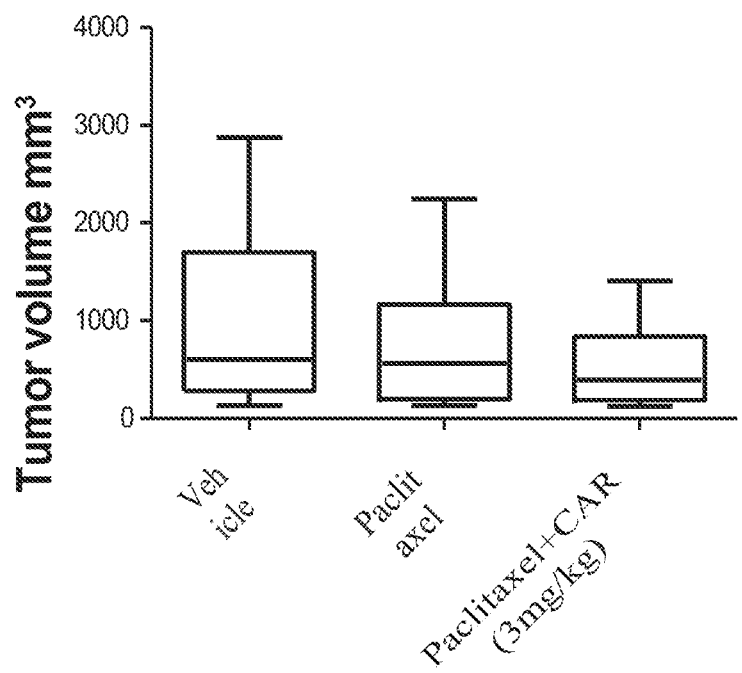

Co-administration of CAR pharmacophore with paclitaxel reduced the mean tumor volume over 15 days compared to paclitaxel alone (FIG. 21) and provided the additional benefit of amelioration of cancer-induced weight loss. CAR pharmacophore treated animals gained 11% relative to their average starting bodyweight while the paclitaxel alone group gained 5% and saline vehicle control group gained 6% after 32 days (data not shown).

Example 12: Selective Drug Efficacy in Pulmonary Arterial Hypertension

PAH was induced in male Sprague-Dawley rats (300-330 g, 10 weeks old, Harlan) with a single intraperitoneal dose of monocrotaline (60 mg/kg). Treatment was initiated four weeks after PAH induction with either imatinib (50 mg/kg or 10 mg/kg) or imatinib (50 mg/kg or 10 mg/kg)+CAR pharmacophore combination (3 mg/kg) for 2 weeks with daily i.v. (FIGS. 22 and 23) or daily sublingual administration.

Figure 22:
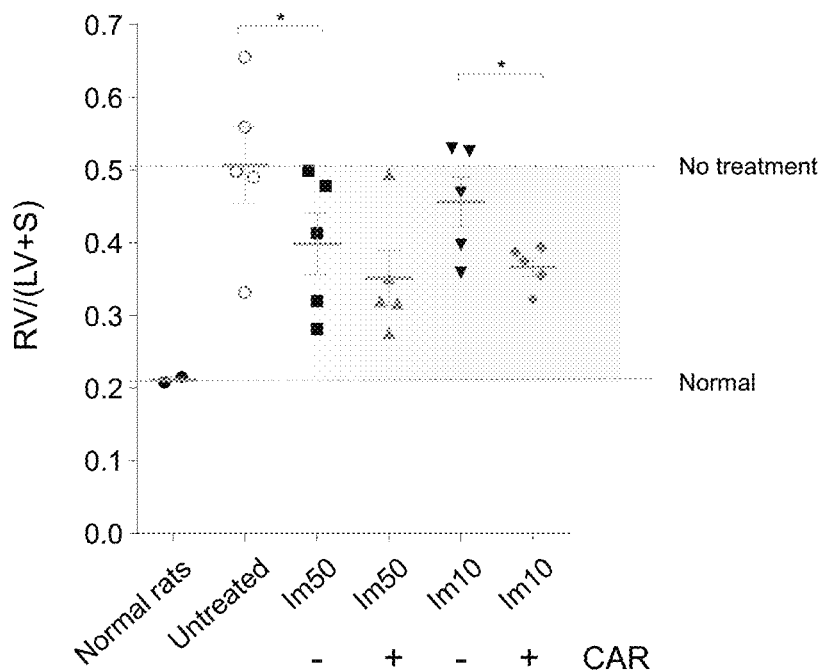
Figure 23:
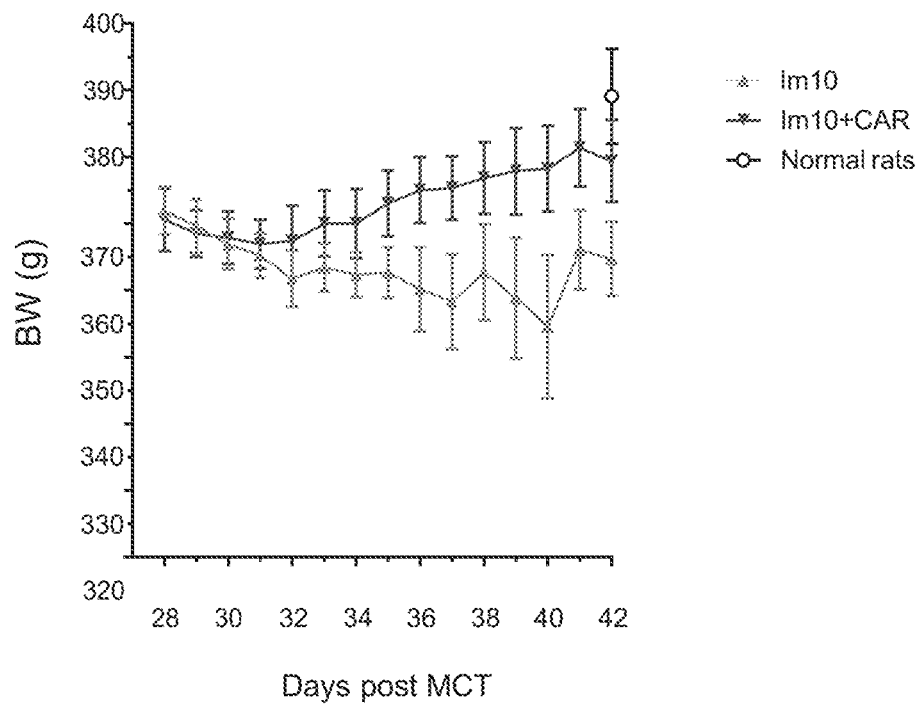
Figure 24:
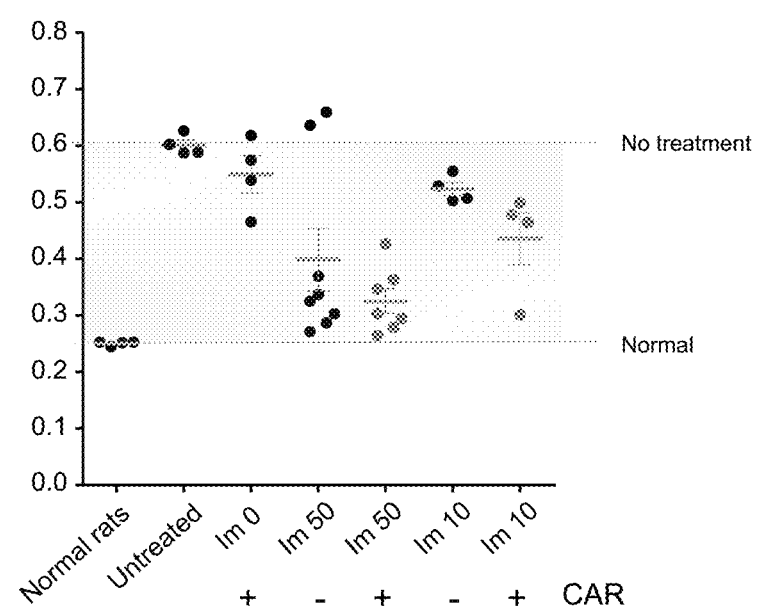
Figure 25:
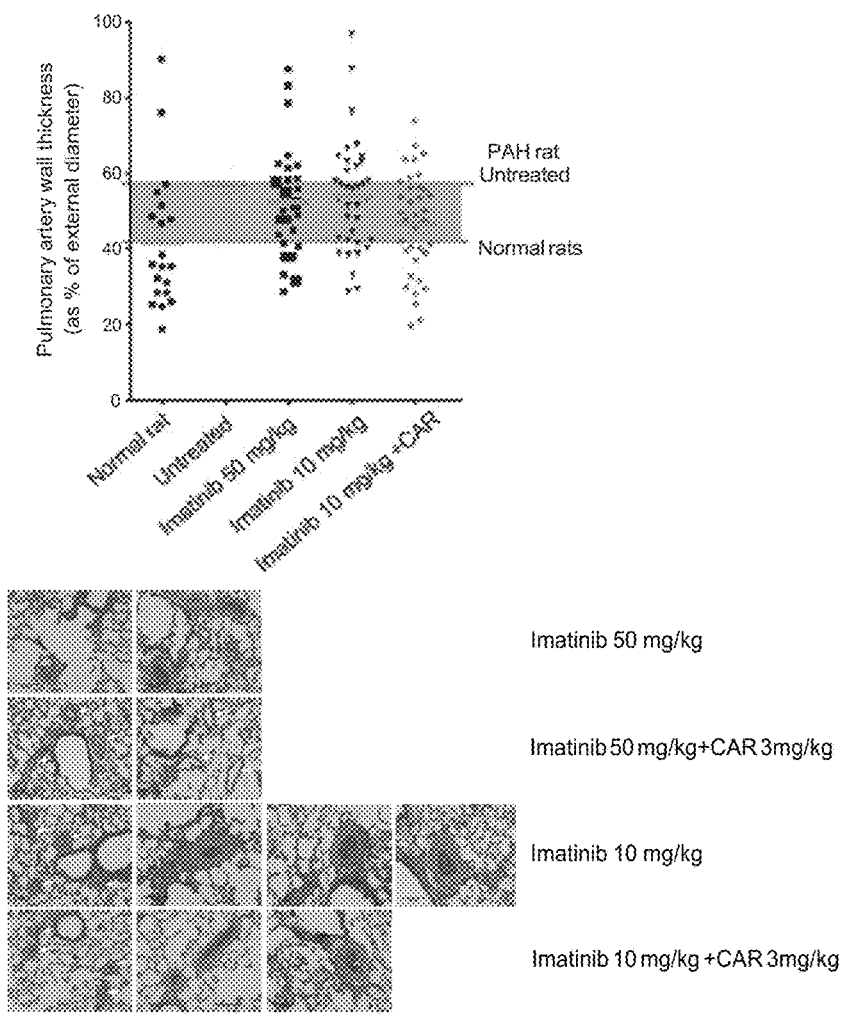
FIG. 25. Effect of CAR pharmacophore on pulmonary artery (PA) muscularization in PAH model rats.

Co-administration of CAR pharmacophore enhanced the therapeutic benefit of imatinib as measured by improvements in right heart hypertrophy (FIGS. 22 and 24) and pulmonary artery muscularization (FIG. 25). Remarkably, even at an 80%-reduced dose of imatinib (10 mg/kg), the addition of CAR pharmacophore adjuvant to the therapy produced an efficacy equivalent to or greater than the efficacy of the full-dose 50 mg/kg imatinib monotherapy (FIGS. 22 and 25). Prolonged intravenous administration of imatinib appears to have a significant adverse effect on bodyweight. Co-administration of CAR pharmacophore peptide appears to alleviate this side effect. Addition of CAR pharmacophore as an adjuvant to the imatinib therapy increased the bodyweight of the MCT rats, indicating considerable improvement in the overall health of the animals.

Glossary

1. DMEM—Dulbecco's Modified Eagle's medium—a cell culture medium that contains amino acids, salts, glucose, and vitamins.
2. FAM—Carboxyfluorescein fluorescent dye used as a tracer agent.
3. DAPI—4',6-diamidino-2-phenylindole—a fluorescent stain that binds strongly to A-T rich regions in DNA, and is used extensively in fluorescence microscopy.
4. NIH—National Institutes of Health
5. STTR—Small Business Technology Transfer—a program sponsored by the NIH that seeks to increase the participation of small businesses in Federal R&D, and to increase private sector commercialization of technology developed through Federal R&D.
6. CAR—Nine-amino acid peptide with sequence CARSKNKDC; may be cyclic or linear.
7. cCAR—Cyclic, nine-amino acid peptide with sequence CARSKNKDC.
8. tCAR—Truncated, linear, seven-amino acid peptide with sequence CARSKNK.
9. SEQ ID NO—Acronym for "Sequence Identification Number," and used to identify certain disclosed sequences.
10. CADD—Computer-aided drug design.
11. CHO-K1—A subclone derivation from the parental Chinese Hampster Ovary cell line; initiated from a biopsy of an ovary of an adult Chinese hamster by T. T. Puck in 1957.
12. FACS—Fluorescence-activated cell sorting.
13. HS—Heparan Sulfate
14. HSA—Human serum albumin.
15. HSA-tCAR—A conjugated compound produced by covalently linking truncated CAR (tCAR; SEQ ID NO: 24) to the free sulfhydryl group at the Cys34 residue of human serum albumin (HSA) via a disulfide bond.
16. ATIII—Antithrombin III
17. AB1—The monoclonal anticancer antibody B1.

18. CAR-AB1—A conjugated compound produced by covalently linking Cyclic CAR (SEQ ID NO: 1) to the Fv fragment of the monoclonal anticancer antibody B1.
19. CNS—Central nervous system
20. Cyclic CAR Rifa—Cyclic CAR Rifabutin peptidomimetic.
21. Cyclic CAR-Rapa—Cyclic CAR-Rapamycin peptidomimetic.
22. Cyclic CAR-Voclo—Cyclic CAR-Voclosporin peptidomimetic.
23. Linear CAR-Rifa—Linear CAR-Rifabutin peptidomimetic.
24. Linear CAR-Rapa—Linear CAR-Rapamycin peptidomimetic.
25. Linear CAR-Voclo—Linear CAR-Voclosporin peptidomimetic.
26. PAH—Pulmonary arterial hypertension
27. DNA—Deoxyribonucleic acid.
28. LPS—Lipopolysaccharide endotoxin
29. MCT—Monocrotaline
30. NMR—Nuclear magnetic resonance.
31. PBS—Phosphate buffered saline
32. Arg—Arginine.
33. His—Histidine.
34. Lys—Lysine.
35. Asp—Aspartic acid.
36. Glu—Glutamic acid.
37. Ser—Serine.
38. Thr—Threonine.
39. Gln—Glutamine.
40. Cys—Cysteine.
41. Gly—Glycine.
42. Pro—Proline.
43. Ala—Alanine.
44. Val—Valine.
45. Ile—Isoleucine.
46. Leu—Leucine.
47. Met—Methionine.
48. Phe—Phenylalanine.
49. Tyr—Tyrosine.
50. Trp—Tryptophan.
51. Log D—the logarithm of partition coefficient (P), which is a measure of the tendency of a compound to partition between lipophilic organic phase and polar aqueous phase.

SEQUENCE LISTING

```
<160> NUMBER OF SEQ ID NOS: 35

<210> SEQ ID NO 1
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide

<400> SEQUENCE: 1

Cys Ala Arg Ser Lys Asn Lys Asp Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Cys Ala Arg Ser Arg Asn Lys Asp Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthesized

<400> SEQUENCE: 3

Cys Ala Arg Ser Lys Asn Arg Asp Cys
1               5

<210> SEQ ID NO 4
<211> LENGTH: 9
<212> TYPE: PRT
<213> ORGANISM: Artificial Sequence
```

```
<220> FEATURE:
<223> OTHER INFORMATION: Synthesized

<400> SEQUENCE: 4

Cys Ala Arg Ser Arg Asn Arg Asp Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized

<400> SEQUENCE: 5

Cys Ala Lys Ser Arg Asn Lys Asp Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized

<400> SEQUENCE: 6

Cys Ala Lys Ser Lys Asn Arg Asp Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthesized

<400> SEQUENCE: 7

Cys Ala Lys Ser Lys Asn Lys Asp Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthesized

<400> SEQUENCE: 8

Cys Ala Lys Ser Arg Asn Arg Asp Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide

<400> SEQUENCE: 9

Cys Ala Arg Ser Lys Asn Lys Asp Cys
1               5

<210> SEQ ID NO 10
```

```
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide

<400> SEQUENCE: 10

Cys Ala Arg Ser Lys Asn Lys Asp Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide

<400> SEQUENCE: 11

Cys Ala Arg Ser Lys Asn Lys Asp Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthesized

<400> SEQUENCE: 12

Cys Ala Arg Ser Lys Asn Lys Asp Cys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthesized

<400> SEQUENCE: 13

Cys Ala Arg Ser Lys Asn Lys Asp Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

Cys Ala Arg Ser Lys Asn Lys Asp Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 15

Cys Ala Arg Ser Lys Asn Lys Asp Cys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide
<220> FEATURE:
<221> NAME/KEY: MISC_FEATURE
<222> LOCATION: (7)..(7)
<223> OTHER INFORMATION: X is equal to D-amino acid K

<400> SEQUENCE: 16

Cys Ala Arg Ser Lys Asn Xaa Asp Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide
<220> FEATURE:
<221> NAME/KEY: MISC_FEATURE
<222> LOCATION: (2)..(2)
<223> OTHER INFORMATION: X is equal to D-amino acid allylglycine

<400> SEQUENCE: 17

Cys Xaa Arg Ser Lys Asn Lys Asp Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide
<220> FEATURE:
<221> NAME/KEY: MISC_FEATURE
<222> LOCATION: (3)..(3)
<223> OTHER INFORMATION: X is equal to D-amino acid N

<400> SEQUENCE: 18

Cys Ala Xaa Ser Lys Asn Lys Asp Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: cyclic peptide
```

-continued

```
<220> FEATURE:
<221> NAME/KEY: MISC_FEATURE
<222> LOCATION: (1)..(1)
<223> OTHER INFORMATION: X is equal to N-methylated C

<400> SEQUENCE: 19

Xaa Ala Arg Ser Lys Asn Lys Asp Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (5)..(5)
<223> OTHER INFORMATION: X is equal to D-amino acid K

<400> SEQUENCE: 20

Cys Ala Arg Ser Xaa Asn Lys Asp Cys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: X is equal to D-amino acid allylglycine

<400> SEQUENCE: 21

Cys Xaa Arg Ser Lys Asn Lys Asp Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: X is equal to D-amino acid N

<400> SEQUENCE: 22

Cys Ala Xaa Ser Lys Asn Lys Asp Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: X is equal to N-methylated C

<400> SEQUENCE: 23

Xaa Ala Arg Ser Lys Asn Lys Asp Cys
1               5
```

```
<210> SEQ ID NO 24
<211> LENGTH: 7
<212> TYPE: PRT
<213> ORGANISM: Artificial Sequence
<220> FEATURE:
<223> OTHER INFORMATION: Synthesized

<400> SEQUENCE: 24

Cys Ala Arg Ser Lys Asn Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (5)..(5)
<223> OTHER INFORMATION: X is equal to D-amino acid K

<400> SEQUENCE: 25

Cys Ala Arg Ser Xaa Asn Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: X is equal to D-allylglycine

<400> SEQUENCE: 26

Cys Xaa Arg Ser Lys Asn Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: X is equal to D-amino acid N

<400> SEQUENCE: 27

Cys Ala Xaa Ser Lys Asn Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: X is equal to N-methylated C

<400> SEQUENCE: 28

Xaa Ala Arg Ser Lys Asn Lys
1               5
```

```
<210> SEQ ID NO 29
<211> LENGTH: 585
<212> TYPE: PRT
<213> ORGANISM: Homo sapiens
<220> FEATURE:
<221> NAME/KEY: SITE
<222> LOCATION: (34)..(34)
<223> OTHER INFORMATION: The thiol of Cys34 of HSA is conjugated to
      thiol of Cys 1 of SEQ ID NO. 24

<400> SEQUENCE: 29

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350
```

```
Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 30
<211> LENGTH: 112
<212> TYPE: PRT
<213> ORGANISM: Artificial Sequence
<220> FEATURE:
<223> OTHER INFORMATION: Synthesized
<220> FEATURE:
<221> NAME/KEY: SITE
<222> LOCATION: (1)..(1)
<223> OTHER INFORMATION: The cyclic CAR peptide is conjugated via amide
      bond between the side chain of Asp1 and the amino group of Cys1 of
      SEQ ID NO. 1

<400> SEQUENCE: 30

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Leu Val His Ser
            20                  25                  30

Asp Gly Lys Thr Tyr Leu His Trp Phe Leu Gln Lys Pro Gly Gln Ser
        35                  40                  45

Pro Thr Leu Leu Ile Tyr Lys Val Ser Asn Arg Phe Ser Gly Val Pro
    50                  55                  60

Asp Arg Phe Ser Gly Ser Gly Ser Gly Thr Asp Phe Ile Leu Lys Ile
65                  70                  75                  80

Ser Arg Val Glu Ala Glu Asp Leu Gly Val Tyr Phe Cys Ser Gln Ser
                85                  90                  95
```

Thr His Val Pro Leu Thr Phe Gly Cys Gly Thr Lys Leu Glu Leu Lys
                100                 105                 110

<210> SEQ ID NO 31
<211> LENGTH: 9
<212> TYPE: PRT
<213> ORGANISM: Artificial Sequence
<220> FEATURE:
<223> OTHER INFORMATION: Synthesized

<400> SEQUENCE: 31

Leu Ala Arg Ser Lys Asn Lys Asp Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthesized

<400> SEQUENCE: 32

Cys Ala Lys Ser Arg Asn His Asp Cys
1               5

<210> SEQ ID NO 33
<211> LENGTH: 9
<212> TYPE: PRT
<213> ORGANISM: Artificial Sequence
<220> FEATURE:
<223> OTHER INFORMATION: Synthesized

<400> SEQUENCE: 33

Cys Ala Arg Ser Lys Asn Lys Leu Cys
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized

<400> SEQUENCE: 34

Cys Gly Gly Gly Gly Gly Gly Gly Cys
1               5

<210> SEQ ID NO 35
<211> LENGTH: 121
<212> TYPE: PRT
<213> ORGANISM: Artificial Sequence
<220> FEATURE:
<223> OTHER INFORMATION: synthized
<220> FEATURE:
<221> NAME/KEY: MISC_FEATURE
<222> LOCATION: (44)..(44)
<223> OTHER INFORMATION: Note: This sequence is the Fv Heavy Chain of
      Anticancer Antibody B1 which is covalently linked via a disulfide
      bond at Cys100 of SEQ ID NO. 30

<400> SEQUENCE: 35

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Asp Asn
            20                  25                  30

Tyr Met Tyr Trp Val Arg Gln Thr Pro Glu Lys Cys Leu Glu Trp Val

```
                    35                  40                  45
Ala Thr Ile Ser Asp Gly Gly Thr Tyr Ile Asp Tyr Ser Asp Ser Val
        50                  55                  60

Lys Gly Arg Phe Thr Ile Ser Arg Asp Asn Ala Lys Asn Asn Leu Tyr
65                      70                  75                  80

Leu Gln Met Ser Ser Leu Arg Ser Glu Asp Thr Gly Met Tyr Tyr Cys
                85                  90                  95

Gly Arg Ser Pro Ile Tyr Tyr Asp Tyr Ala Pro Phe Thr Tyr Trp Gly
            100                 105                 110

Gln Gly Thr Leu Val Thr Val Ser Ala
            115                 120
```

We claim:

1. A pharmacophore for administration to an individual suffering from a disease, wherein the pharmacophore comprises a peptide comprising the amino acid sequence selected from the group consisting of SEQ ID NOs: 2-8.

2. The pharmacophore of claim 1, wherein the disease is selected from the group consisting of pulmonary arterial hypertension, sepsis, kidney disease, cancer and cachexia.

* * * * *